(12) United States Patent
Kleefstra et al.

(10) Patent No.: US 11,885,823 B2
(45) Date of Patent: *Jan. 30, 2024

(54) SYSTEM AND METHOD FOR INCUBATION AND READING OF BIOLOGICAL CULTURES

(71) Applicant: BD KIESTRA B.V., Drachten (NL)

(72) Inventors: Martijn Kleefstra, Surhuisterveen (NL); Martijn Xander Berntsen, Leeuwarden (NL); Jan Bart Van Der Vijver, Groningen (NL); Tsjerk Nauta, Breda (NL); Andrej Girgenson, Hurdegaryp (NL)

(73) Assignee: BD KIESTRA B.V., Drachten (NL)

( * ) Notice: Subject to any disclaimer, the term of this patent is extended or adjusted under 35 U.S.C. 154(b) by 211 days.

This patent is subject to a terminal disclaimer.

(21) Appl. No.: 17/320,955

(22) Filed: May 14, 2021

(65) Prior Publication Data

US 2021/0270862 A1 Sep. 2, 2021

Related U.S. Application Data

(63) Continuation of application No. 14/687,400, filed on Apr. 15, 2015, now Pat. No. 11,041,871.

(Continued)

(51) Int. Cl.
*C12M 1/00* (2006.01)
*C12M 1/36* (2006.01)
(Continued)

(52) U.S. Cl.
CPC ............. *G01N 35/04* (2013.01); *C12M 23/44* (2013.01); *C12M 41/14* (2013.01); *C12M 41/48* (2013.01);
(Continued)

(58) Field of Classification Search
CPC ............. G01N 35/04; G01N 35/00732; G01N 35/0099; G01N 35/0092; G01N 35/028;
(Continued)

(56) References Cited

U.S. PATENT DOCUMENTS 4,250,266 A 2/1981 Wade
4,720,463 A 1/1988 Farber
(Continued)

FOREIGN PATENT DOCUMENTS

EP 2497823 B1 8/2017
WO 2015114121 A1 8/2015
WO 2016172527 A2 10/2016

OTHER PUBLICATIONS

Bourbeau, Paul, "Total Lab Automation in Microbiology: Much closer than you might think", Sep. 6, 2012, 11 pages.
(Continued)

*Primary Examiner* — Liban M Hassan
(74) *Attorney, Agent, or Firm* — Botos Churchill IP Law LLP

(57) ABSTRACT

The present invention describes an integrated incubator and image capture module that regulates the incubator atmosphere and obtains high-resolution digital images of sample specimens. The incubator has a cabinet type enclosure that enables the provision of a controlled environment to the contents of the incubator by having at least three ports on one face of the cabinet for the passage of sample containers. Additionally, an image capture module is located immediately adjacent to the incubator. In this regard, using at least three separate access/egress points for the sample containers streamlines operation of the system and enhances preservation of the incubator environment. Furthermore, locating the image capture module directly adjacent to the incubator reduces the amount of time a sample container is exposed to the external environment, thereby reducing the extent to (Continued)

which samples are exposed to potential contaminants and reducing the exchange of the lab and ambient atmospheres.

13 Claims, 17 Drawing Sheets

Related U.S. Application Data

(60) Provisional application No. 61/980,272, filed on Apr. 16, 2014.

(51) Int. Cl.
    *C12M 3/00*     (2006.01)
    *G01N 35/00*     (2006.01)
    *G01N 35/04*     (2006.01)
    *G01N 35/02*     (2006.01)

(52) U.S. Cl.
CPC ... *G01N 35/0099* (2013.01); *G01N 35/00732* (2013.01); *G01N 35/0092* (2013.01); *G01N 35/028* (2013.01); *G01N 2035/00277* (2013.01); *G01N 2035/00287* (2013.01); *G01N 2035/00316* (2013.01); *G01N 2035/00356* (2013.01); *G01N 2035/00831* (2013.01); *G01N 2035/00851* (2013.01); *G01N 2035/0405* (2013.01); *G01N 2035/0427* (2013.01); *G01N 2035/0441* (2013.01); *G01N 2035/0465* (2013.01); *G01N 2035/0493* (2013.01); *G01N 2035/0496* (2013.01)

(58) Field of Classification Search
CPC .......... G01N 2035/00277; G01N 2035/00287; G01N 2035/00316; G01N 2035/00356; G01N 2035/00831; G01N 2035/00851; G01N 2035/0405; G01N 2035/0427; G01N 2035/0441; G01N 2035/0465; G01N 2035/0493; G01N 2035/0496; C12M 23/44; C12M 41/14; C12M 41/48
See application file for complete search history.

(56) References Cited

U.S. PATENT DOCUMENTS

| | | |
|---|---|---|
| 7,596,251 B2 | 9/2009 | Affleck et al. |
| 2002/0064867 A1 | 5/2002 | Clark et al. |
| 2003/0040104 A1 | 2/2003 | Barbera-Guillem |
| 2007/0020748 A1 | 1/2007 | Motegi et al. |
| 2010/0291619 A1 | 11/2010 | Robinson |
| 2010/0330654 A1 | 12/2010 | Van et al. |
| 2012/0034596 A1 | 2/2012 | Seidl et al. |
| 2014/0045210 A1 | 2/2014 | Menges et al. |
| 2015/0299639 A1 | 10/2015 | Kleefstra et al. |
| 2016/0083686 A1 | 3/2016 | Triva |
| 2017/0257539 A1 | 9/2017 | Kokubo |

OTHER PUBLICATIONS

International Search Report and Written Opinion for International Application No. PCT/EP2021/076969 dated Jan. 14, 2022.

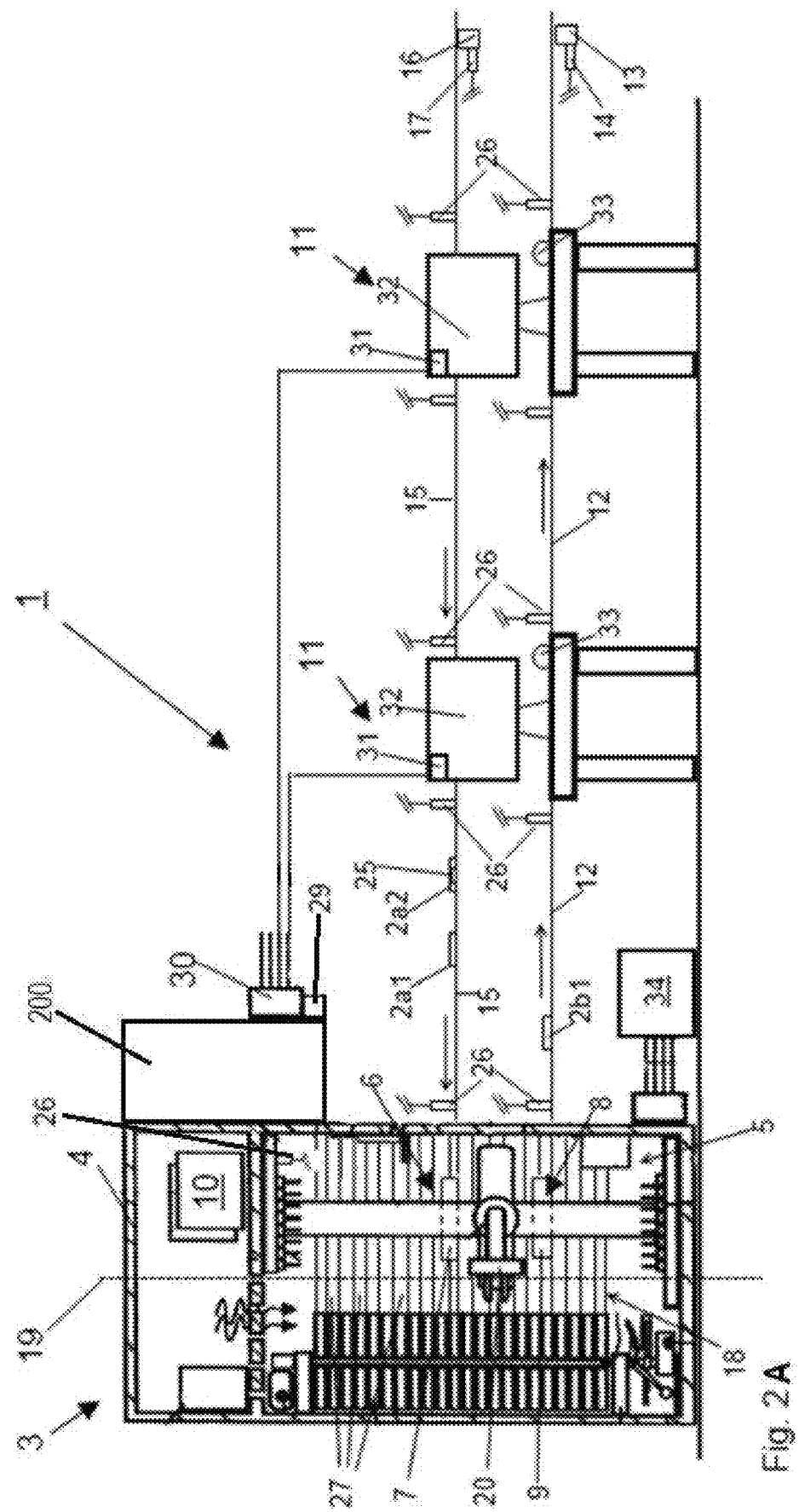

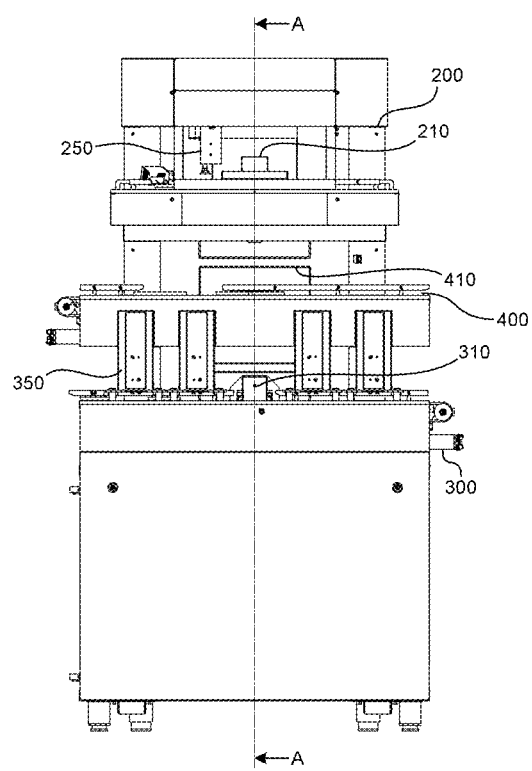
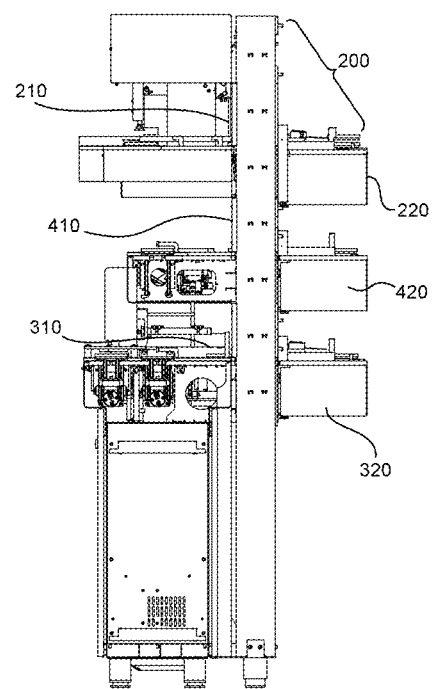
FIG. 7A                                    FIG. 7B

SYSTEM AND METHOD FOR INCUBATION AND READING OF BIOLOGICAL CULTURES

CROSS-REFERENCE TO RELATED APPLICATIONS

This application is a continuation of U.S. application Ser. No. 14/687,400, filed on Apr. 15, 2015, allowed, which application claims the benefit of the filing date of U.S. Provisional Patent Application No. 61/980,272 filed Apr. 16, 2014, the disclosures of which are hereby incorporated herein by reference.

BACKGROUND OF THE INVENTION

Field of the Invention

The present invention relates to a method and system for incubating and analyzing biological samples.

Description of the Related Art

Sample incubators are used to grow and maintain microbiological and cell cultures prepared from biological samples for research and analysis in a number of fields. The simplest incubators are insulated boxes that work by controlling a number of environmental factors, including temperature and humidity to provide an environment suitable to maintain sample viability and/or to support microbial growth. Incubators also have features that control the composition of the atmosphere in the incubator, such as the amount of carbon dioxide and/or oxygen in the incubator environment.

One problem with incubators is the difficulty in maintaining the controlled atmosphere when samples are retrieved from the incubator. Typically, containers that contain growth media inoculated with sample such as, e.g., petri dishes, have a culture media that provides nutrients that support microbial growth therein. In addition to the nutrients, the media often has other additives (e.g. sodium chloride) that will provide the culture media with the correct consistency to support the growth of target microorganisms, or nutrient indicators that will indicate target microorganisms, if present in the sample. One challenge for incubators with controlled atmospheres is maintaining the controlled atmosphere when the sample is inserted, removed from or replaced into the incubator as the sample is evaluated to determine the presence of absence of microorganisms in the sample.

In a simple incubator, a single door or hatch located on one side, or the top, of the incubator enclosure is provided to access the contents of the incubator, either to place samples in the incubator or remove them therefrom. This results in a significant loss of the incubator's controlled atmosphere to the larger environment, typically a laboratory environment, in which the incubator is placed. Also, opening the door allows the ambient atmosphere to enter the incubator. The loss of the controlled environment in the incubator enclosure can retard microbial growth in the culture media or contaminate the specimen.

Additionally, removing the sample containers from the incubator for an extended period of time, for example to electronically image the sample culture to detect microbial growth, could negatively impact the growth of the target microorganisms or expose the specimens to contaminants in the lab, which can adversely affect the integrity of the assay results.

One example of a commercially available system for incubation and imaging is the BD Kiestra™ ReadA™. The BD Kiestra™ ReadA™ system uses a series of tracks to move plates within the incubator. During and after incubation, the plates are removed and are optionally inspected by optical imaging for evidence of microbial growth. The images of the plates taken during incubation are compared to determine growth results.

Thus, there is a need in the art for systems that provide monitoring capabilities for cultures under incubation that maintain the integrity of the incubator's controlled atmosphere and reduce the amount of time a specimen being incubated/cultured is exposed to lab conditions with little to no operator intervention. Furthermore, there is a need to more efficiently manage the flow of plated cultures into and out of the incubator yet preserve the controlled environment in the incubator as plated cultures are placed in and removed from the incubator for processing.

BRIEF SUMMARY OF THE INVENTION

The present invention addresses the above problems by providing an intelligent incubation and imaging system that combines regulating the incubator atmosphere with automatic, high-resolution digital imaging. Moreover, the combined incubator and imaging system described in the current application can fit seamlessly into an automated lab environment or be a stand-alone unit working with a lab operator.

The incubator has a cabinet type enclosure that enables the provision of a controlled environment to the contents of the incubator. Typically, the contents of the incubator are containers such as petri dishes that contain nutrient media that has been inoculated by a biological or environmental sample. The nutrient media and controlled atmosphere provided to the incubator support the growth of at least certain microbes in the media if present in the sample with which the media has been inoculated.

Structurally, one face of the incubator has hatches or doors located thereon as dedicated ports for automated placement and removal of samples from the incubator cabinet. Typically, the incubator cabinet has multiple ports to facilitate ingress and egress of petri dishes into and out of the cabinet. In one embodiment described herein the cabinet has at least three such ports, preferably all located on the same side of the cabinet (referred to as the first face of the cabinet). These ports are referred to as doors herein to reflect the fact that the ports open and close to preserve the cabinet environment as the petri dishes enter into or are removed from the cabinet. According to some embodiments, each door may include separate ports for ingress and egress of the sample containers. In other embodiments, a port may have more than one door for ingress and egress of the sample containers. Doors, as used herein, are one example of a port that will open to allow an article, such as a sample container, to be conveyed through the door and close after such passage.

In certain embodiments the ports are configured as doors., The first port may be a door dedicated to accepting automated delivery of sample containers (e.g. petri dishes) into the incubator cabinet. As such, the samples are conveyed to the door, which opens when a sensor indicates the presence of a container to be transported into the cabinet. In one embodiment, the sensor communicates the presence of the sample container to a processor, which then communicates with the door actuator. The door opens automatically and the sample is transferred from the external conveyer to an internal apparatus that places the sample container in a location within the incubator that is associated with the sample. Software is used to track the placement of the sample in the incubator, the sample container having a machine readable tag (e.g. a barcode, RFID tag, label, etc.) that enables the location of the sample in the incubator to be known at all times using a reader for that tag and a robotic mechanism for the controlled placement and retrieval of the sample containers in the incubator environment. Conveyers and robotic mechanisms for controlled movement and placement of sample containers is well known to one skilled in the art and not described in detail herein.

The second port or door may be a dedicated door through which sample containers are finally removed from the incubator. By final removal it is meant that the system has determined that the residence time of the sample in the incubator has ended, where such end-point may be based on expiration of an incubation time or may be based on feedback from the imaging process unit detailed below. Upon removal, the samples may be moved to disposal (e.g., if no growth has occurred), may be retrieved by an operator, or maybe moved in an automated manner to a downstream analysis module or instrument.

The third port or door may be a dedicated single door to an automated electronic image capture module or it can be multiple ports or doors. As noted above, the third port may include individual ports for ingress and egress of the sample containers. For example, the third door may include a dual door construction that includes a first door through which sample containers enter the image capture module and a second door through which sample containers exit the image capture module. Accordingly, the image capture module may receive samples from the incubator for inspection to ascertain if the sample has changed over time, e.g. if microbial growth has occurred in the sample. The module is enclosed and sample containers are transported directly into the module from the cabinet and are directly returned to the cabinet using a conveyer disposed in the image capture module.

In one embodiment, the incubator also includes a robotic arm for handling and moving the one or more containers amongst the three doors of the incubator and within the incubator itself. By using such a robotic arm, in particular in combination with the automated conveyor systems and the automated in-feed conveyor, the throughput of cell culture devices can be increased even further. Preferably, the incubator includes a plurality of positions (i.e. slots or shelving).

In an alternate embodiment, the incubator may also include a waste removal station that includes a waste removal outlet separate from the three doors in the face of the incubator. In this regard, the waste removal station includes a waste transportation element for transporting a container marked for removal to the waste removal station via the waste removal outlet. By providing a separate waste removal outlet the removal of the waste containers from the incubator can be performed such that it does not interfere with the discharge of useful containers from the incubator via the second door. In this regard, the throughput of containers is increased even further. In addition by providing a separate waste removal outlet the removal of containers from the incubator can reduce the risk of incubator contamination and contamination of other specimen containers. Additionally, the waste removal outlet helps to maintain the controlled environmental conditions within the incubator.

The image capture module is an enclosed unit immediately adjacent to the incubator. This enables direct transport of the sample from the incubator into the environment of the image capture module with no transport through one or more intervening environments. As noted above, sample containers, such as petri dishes, are conveyed into the image capture module through the third port, or an ingress door of the third port. Thereafter, a lid of the sample container may be removed such that an image capture unit may electronically image (e.g. digitally photographs) the sample container. The lid may be replaced after the sample container has been imaged and the sample container may be conveyed back through the same third door, or alternatively through an egress door of the third port, for placement back into the controlled incubator environment to continue incubation.

Having at least three separate access/egress points for the sample containers to enter into and be removed from the incubator cabinet provides many advantages to automated incubator operation. Examples of such advantages include streamlined operation due to separate conveyor tracks for separate functions, enhanced preservation of incubator environment because the amount of time any single door is open to the external environment is reduced compared with configurations with fewer doors and comparable capacity and functionality. Moreover, having the image capture module directly adjacent to the incubator reduces the amount of time the sample container is exposed to an external environment (with its lack of precisely controlled temperature and atmosphere and potential contaminants) while the sample container is imaged. Since the image capture module is enclosed, it acts as a shield between the lab atmosphere and the incubator atmosphere reducing the extent to which the lab atmosphere enters the incubator and the sample containers enter from the incubator and return thereto through the third door.

Further advantages will be realized by various aspects of the invention and will be apparent from the following detailed description. One of the advantages of the system described herein is the integration with automated platforms for plate inoculation, providing end-to-end automation for inoculation of sample onto plated media, streaking of sample on to media and incubation of inoculated media for growth of target microorganisms. The present system is flexible and can also handle plated media that have been inoculated manually.

BRIEF DESCRIPTION OF THE DRAWINGS

The invention will be better understood from the Detailed Description of the Preferred Embodiments and from the appended drawings, which are meant to illustrate and not to limit the invention, and wherein:

FIGS. 2A and 2B are cross-sectional views of different embodiments of the schematic representation of FIG. 1;

FIG. 7A is a front view of the integrated incubator and image capture module with external conveyors shown in the foreground;

FIG. 7B is a side view of the external conveyors and an image capture module with a portion of the incubator cut away to reveal the portions of the conveyors that extend into the incubator cabinet;

DETAILED DESCRIPTION

Figure 1:
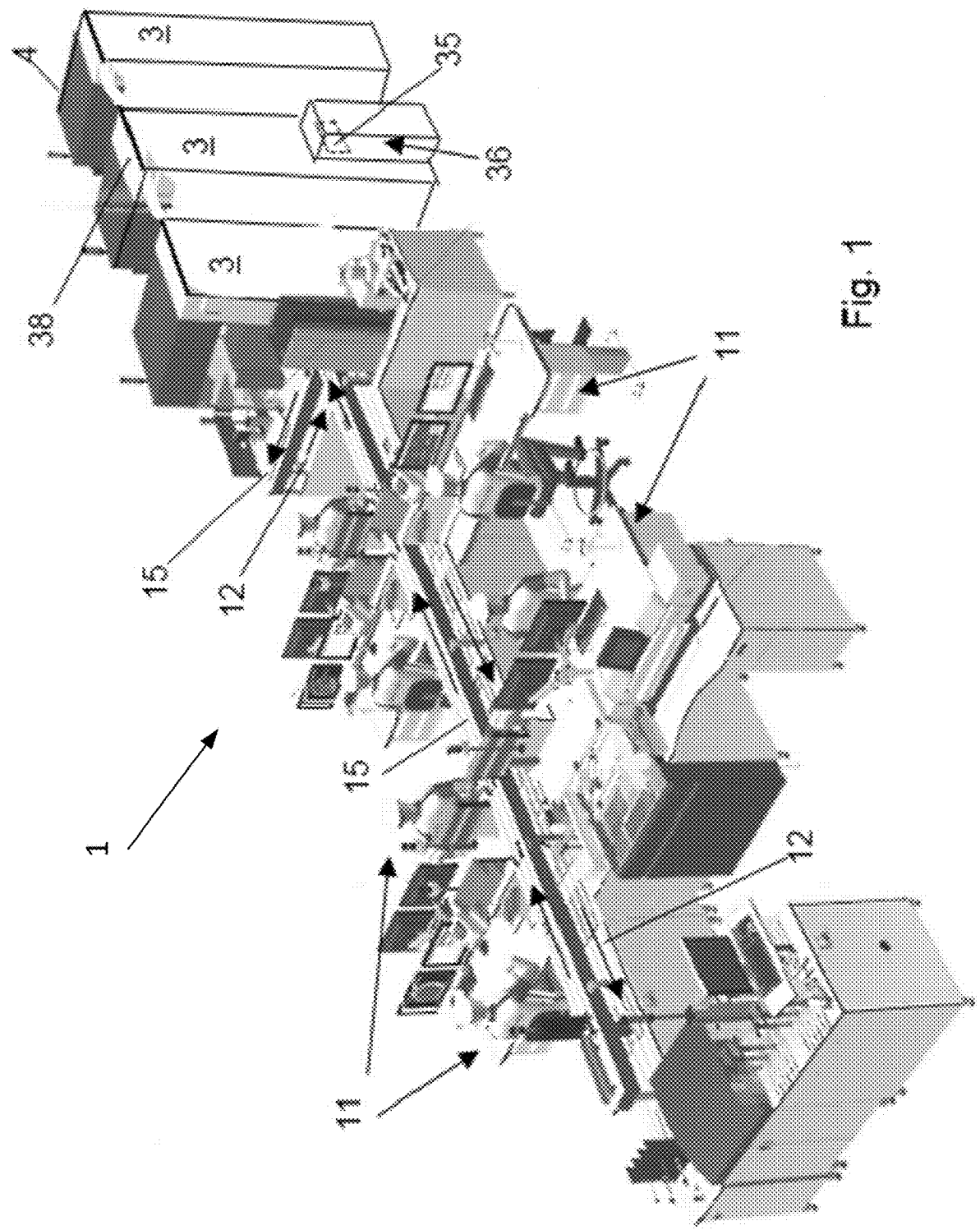
FIG. 1 is a perspective view of a system for automated management and processing of containers for culture growth.
Figure 2B:
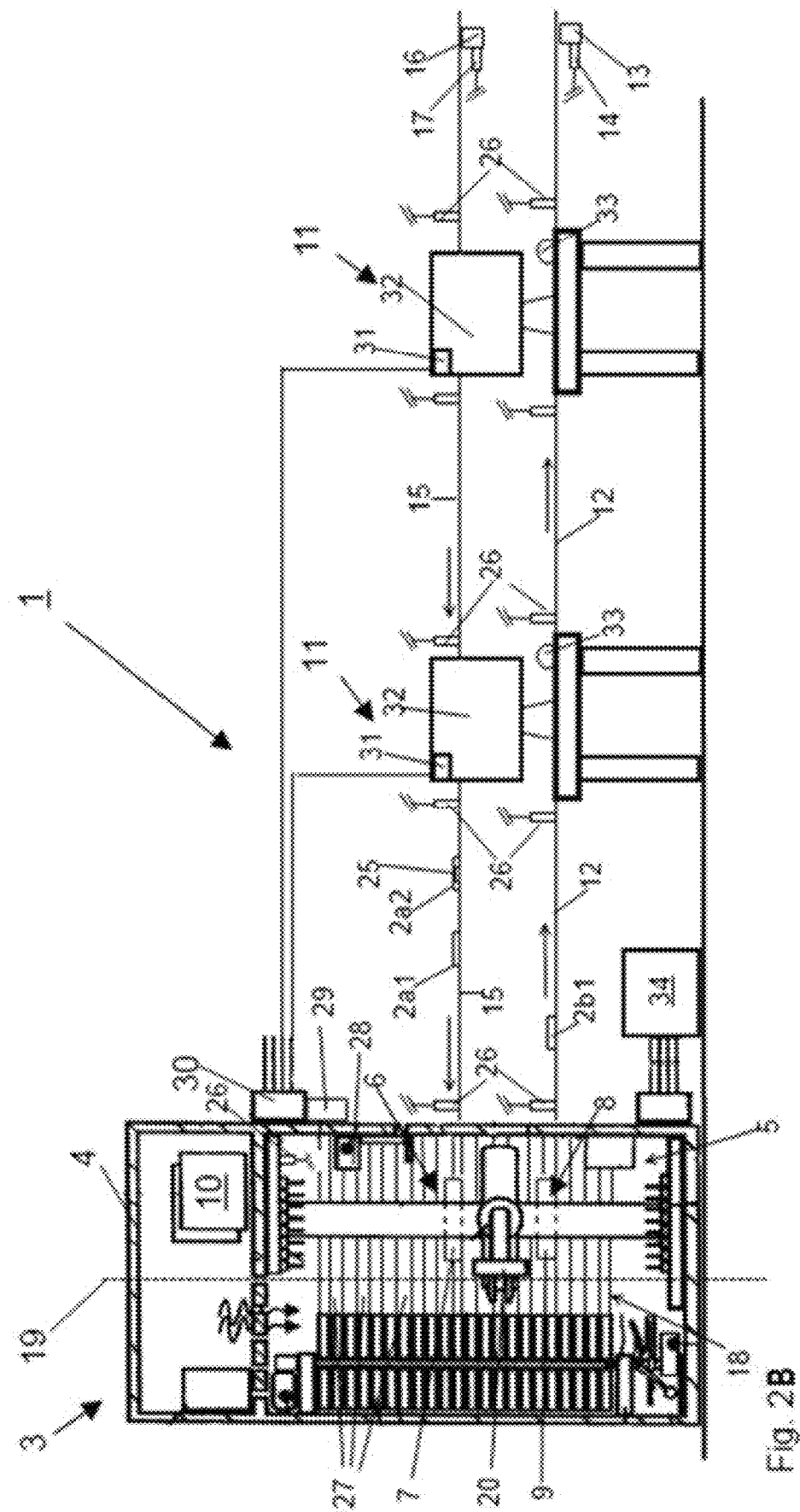

FIGS. 1, 2A, and 2B illustrate a perspective view and schematic representation of different embodiments of a system 1 for automated management of sample containers such as plated media according to the present invention is shown. The system 1 includes at least one integrated incubator and image capture module 3. The integrated incubator and image capture module 3 includes a housing 4 having an incubation chamber 5 that controls environmental conditions such that inoculated containers 2 can be cultured in a controlled manner. The integrated incubator and image capture module 3 as illustrated in FIGS. 1 and 2 also includes a loading station 6 having a first door 7 for receiving inoculated containers 2a into the incubation chamber 5. In the illustrated embodiment, a discharge station 8 having a second door 9 separate from the first door 7 is provided to allow for the discharge of incubated inoculated containers 2b from the incubation chamber 5.

As seen from the embodiment shown in FIGS. 1 and 2, the first door 7 and the second door 9 are provided on the same side of the incubation chamber 5. A discharge door 9 is located on the housing, opposite the first door 7. In alternative embodiments, different locations for the first, second and third doors and the discharge door are contemplated.

In the illustrated embodiment, the first door 7 and the discharge door 9 are closable. In this embodiment, a microprocessor 10 controls door operation. However, alternative embodiments may include a sensor proximately located to the door to control the opening and closing of the doors located on the housing 4.

As noted above, in described embodiments the integrated incubator and image capture module 3 has a microprocessor 10 that controls functions and allows for programmable operation of all the components of the integrated incubator and image capture module 3. In the illustrated embodiments, the microprocessor 10 is provided within the housing 4 as illustrated in FIGS. 1 and 2. However, one of ordinary skill in the art will recognize that the microprocessor 10 may be external to the housing 4 and control the integrated incubator and image capturing module 3 via a data link, such as a direct connection (i.e., USB), a wireless connection, or over a network.

In the illustrated embodiments, the system 1 for automated management of containers 2 includes at least one evaluation station 11. As illustrated, the system 1 may have a plurality of evaluation stations 11. The evaluation stations 11 are located remotely from the integrated incubator and image capture module 3.

In this regard, an automated transfer conveyor 12 conveys the incubated inoculated containers 2b from the discharge station 8 of the integrated incubator and image capture module 3 to the evaluation stations 11. A transfer conveyor controller 13 is provided to control the operations of the transfer conveyor 12. In this regard, the transfer conveyor controller 13 advantageously communicates with relevant components of the system 1 via an interface 14.

In the illustrated embodiments, the system 1 further comprises an automated in-feed conveyor 15 for transporting inoculated contains 2a to the loading station 6 of the integrated incubator and image capture module 3. An in-feed conveyor controller 16 communicates with the in-feed conveyor 15 and the various components of the system 1 via an interface 17.

Referencing FIG. 2A, the integrated incubator and image capture unit 3 includes a storage array 18 within the housing 4 for accommodating a plurality of inoculated containers 2. Preferably, the storage array 18 is partially cylindrical and defines a virtual vertical axis 19. The housing 4 may include a plurality of the storage arrays 18 arranged along its interior walls. Typically, the housing includes between 500 and 2000 positions (i.e., slots or shelving) each adapted to receive and hold an inoculated container 2. In some embodiments, each position of the plurality of positions of the storage array 18 includes a coordinate representative of that position to distinguish from other positions. The storage array will be discussed further with respect to FIG. 5A.

In the illustrated embodiment, a robotic arm 20 is mounted within the housing 4 for handling and moving containers 2 from the first door 7 to one of the plurality of positions. Additionally, the robotic arm 20 may move a container 2 from a position to the second door 9 and, if necessary, between different positions of the storage array 18. The robotic arm 20 will be discussed in greater detail with respect to FIGS. 5B and 6.

Figure 6:
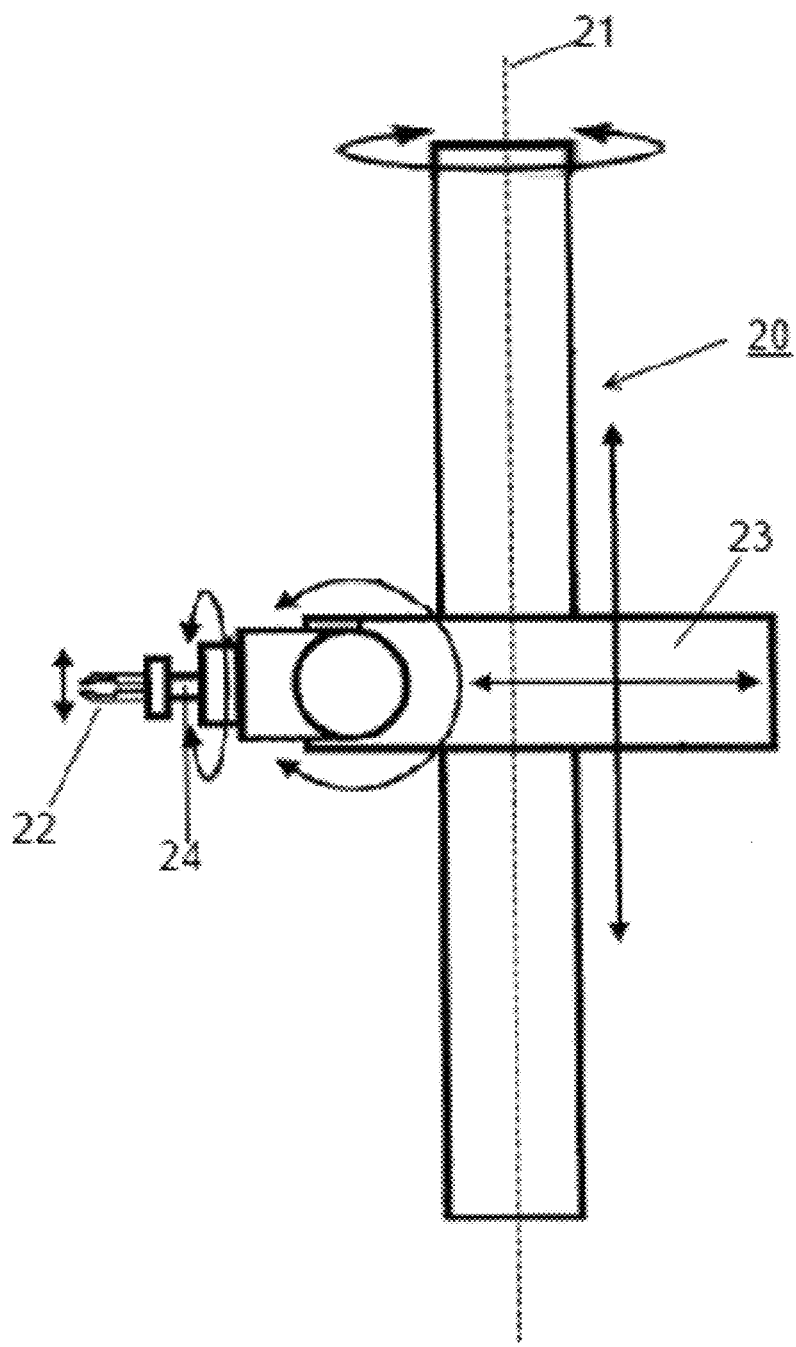
FIG. 6 is a schematic of the robotic arm used to manage the containers.

In operation, the robotic arm 20 is configured to move in a direction along an axis 21, which is parallel to the vertical central axis 19. The robotic arm 20 includes a mechanical gripper 22 and a translational arm 23. The gripper 22 is mounted on the translational arm 23 by a translational joint 24. Alternatively, multiple translational joints may be used. For example, as illustrated in FIG. 6, the gripper 22 is mounted to the translational arm 23 by a translational joint 24 that moves the gripper 360°. The translational arm 23 may also include an additional translational joint to move the gripper in the vertical axis. One of ordinary skill in the art would recognize that the range of motion of the gripper function is a design choice and the various configurations would be readily apparent by the embodiments described herein.

In the illustrated embodiment, the system 1 further comprises a mechanism for tracking containers within the system 1. Each container 2 may include identification information or code 25 for identifying a specific container 2. Such an identification code 25 may include a label, a bar code, a number, a series of numbers, a color, a series of colors, a letter, a series of letters, a symbol, a series of symbols, an RFID tag, a NFC chip, or any combination thereof.

The identification code 25 may be read by a plurality of readers 26 positioned at strategic positions within the system 1. In this regard, the identification code 25 is advantageously used to track (e.g., one or more of locating, identifying, identifying the position of as relative to a point of origin, or cataloging (keeping a record of)) the container 2. The identification code 25 of each container 2 in the system 1 is unique to the container bearing the identification code. Thus, every container in the automated container management system 1 may be distinguished from other containers. In some embodiments, the mechanism for tracking containers 2 may include one or more position sensors 27, placed in the incubation chamber 5 that may be used to correlate a specific coordinate with a specific position within the incubation chamber 5.

In some embodiments, the integrated incubator and image capture module 3 includes an image capture module 200 configured to capture an image of a container 2. According to this embodiment, the microprocessor 10 may issue a command for obtaining an image of a container. The microprocessor 10 causes the robotic arm 20 to pick up the container 2 from its position within the storage array 18. After removing the container 2 from its position, the robotic arm 20 places it on shelf 220 (FIG. 7B) so that the image capture module 200 may obtain an image of said container 2. The image capture module 200 is described in greater detail below.

The obtained image can be outputted via a line 29 and an interface 30 to an evaluation station 11. As illustrated, the line and interface are shown external to the image capture module 200. Further, one of ordinary skill in the art would recognize that the interface 30 may be internal to the image capture module 200. Further, one of ordinary skill in the art would also recognize that the line 29 may be any type of data link, wired or wireless, used to communicate the captured image to the evaluation station 11.

Alternatively, as shown in FIG. 2B the image capture module 200 may be located inside the housing 4 of the integrated incubator and image capture module 3. According to this embodiment, the microprocessor 10 issues a command for obtaining an image of a container. The microprocessor 10 controls the robotic arm 20 such that a container is picked up from its position within the storage array 18. The robotic arm 20 then moves the container to the image obtaining device 28 for obtaining an image of said container. The obtained image may be outputted via a line 29 and an interface 30 to an evaluation station 11. As discussed above, the evaluation station 11 includes an interface 31 and a display device 32 for receiving and displaying the outputted image of the container.

As noted above, the evaluation station 11 may include an interface 31 and a display device 32 connected to the image capture device 200 for receiving and displaying the outputted image of the container 2.

In some embodiments, the evaluation stations 11 may include a tagging device. The tagging device is operatively connected to the microprocessor 10 of the intelligent incubator and image capture module 3. According to this embodiment, a tagging device is formed by an input device 33 at each evaluation station 11. In this regard, the input device 33 may be directly connected to the microprocessor 10 or indirectly connected to the microprocessor 10 via a central system control computer 34. The input device 33 may typically be a key board, a computer mouse, a track ball, a touch screen display, or any other known device capable of making a mark.

Figure 3:
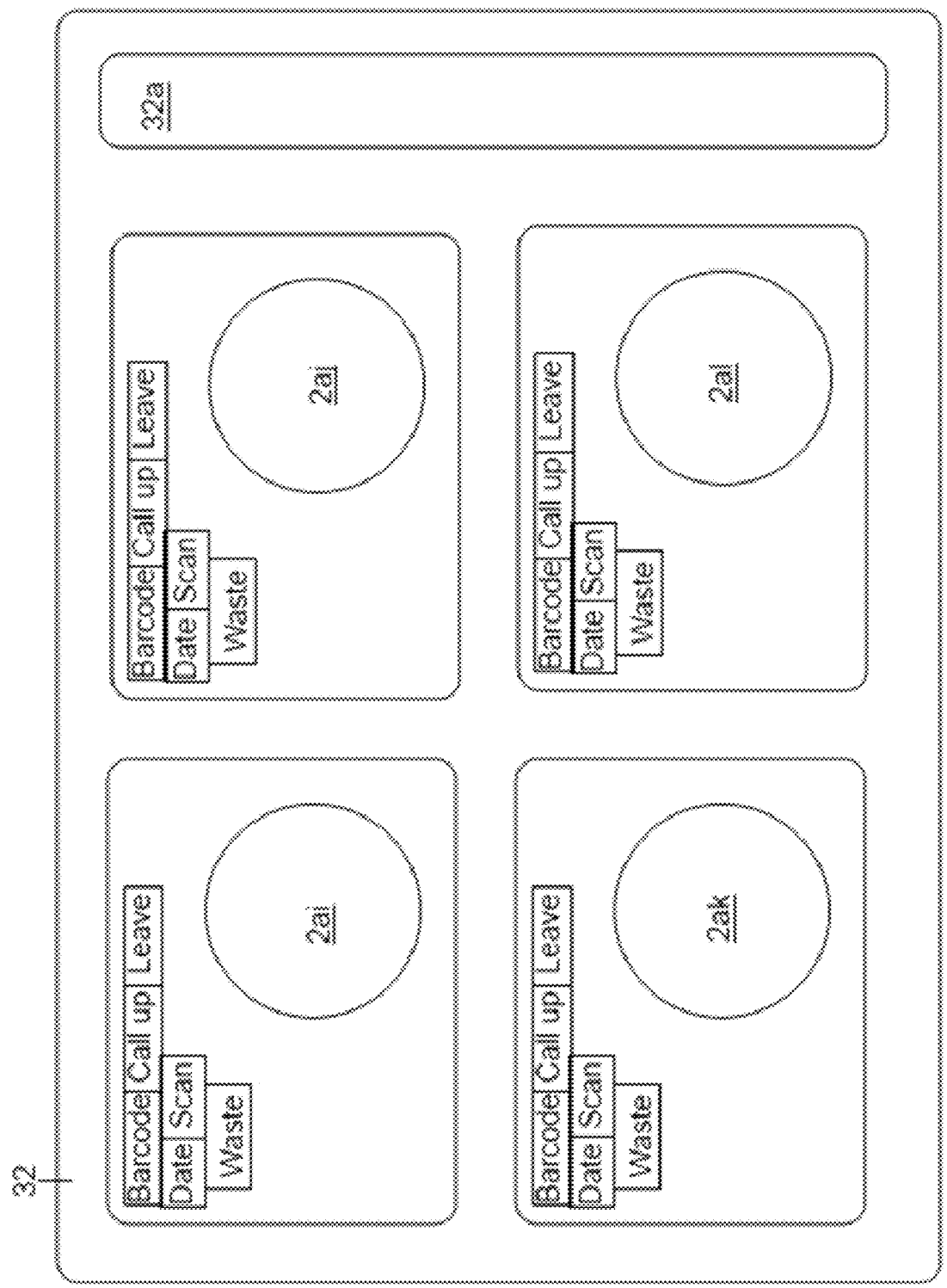
FIG. 3 is an exemplary screen shot for the image capturing and analysis of the captured images.

Turning to FIG. 3, an example of associating a tag with a container 2 is shown. Typically, an image of the container is displayed on the display 32. Typically, the display 32 shows images of four containers 2ai, 2aj, 2ak, 2al. One of ordinary skill in the art will recognize that the number of containers shown on display 32 is a design choice. In this regard, one of ordinary skill in the art would recognize that more or fewer images of containers may be shown on display 32.

For each container displayed on the display 32 of FIG. 3, a number of windows are displayed containing additional information related to the sample. For example, information regarding the identity of the container (i.e., indicated by the box "Barcode"), the date (and optionally the time) on which the container was placed in the incubation chamber 5 (indicated by the box "Date") may be displayed to the lab operator. Certain information, such as the Barcode and Date information, cannot be changed by an operator, and are instead updated by the automated container management system 1.

In some embodiments, other operational boxes may be displayed which may indicate further processing to be performed on the particular container 2. For example, the operations "Call up," "Leave," "Scan," and "Waste" are available to the lab operator. By moving the input device 33 to one of these additional operational box and choosing the operation mentioned therein (i.e., clicking or marking the box), the particular container 2 is tagged and data indicating the tag is sent to the microprocessor 10 (or central system control computer 34). The system then performs the selected operation on the container 2 automatically.

For example, if the container 2ai is tagged with the operation Scan, the robotic arm 20 moves the container 2ai to the reader 26 within the incubation chamber 5 to confirm the identity of the container. Additionally, when the operation Call up is selected for the container 2aj, the container 2aj is moved by the robotic arm 20 towards the discharge station 8, and is subsequently transported out of the incubation chamber 5 via the second door 9. The container 2aj may be transported to an evaluation station 11 where the tagging was performed via the automated transfer conveyor 12.

In another example, the container 2ak is tagged with the operation Leave, then the container 2ak is to remain in the incubation chamber 5. Optionally, when the Leave operational box is selected, a new window may pop-up to indicate a number of choices for the additional time the container 2ak is to remain in the incubation chamber 5. Further, the display 32 may have a pop-up window that allows the lab operator to set the expiry time of the container 2ak. At the expiry time, the robotic arm 20 moves the container 2ak to the image obtaining device 28 to obtain a new image of the container. The captured image is typically displayed on a display 32 of an evaluation station 11.

Referring to the container 2al, the Waste tag is selected. According to this option, a signal is sent to the microprocessor 10 which is arranged for controlling the integrated incubator and image capture module 3 to remove the container 2al. According to some embodiments, the container 2al may be discharged via the second door 9 and removed from the system 1 by a separate sorting unit (not shown). Alternatively, the container 2al may be removed from the incubator via a waste removal outlet 35, separate from the three doors in the face of the incubator. The waste removal outlet 35 may connect to a waste removal station 36 separate from the incubation chamber 5.

One of ordinary skill in the art would recognize that the layout of the display 32 may be altered to suit the needs of the individual lab operators. Arranging different layouts is well known to those skilled in the art and will not be discussed in greater detail herein. Additionally, the operations set forth above are merely illustrative, and one of ordinary skill in the art would recognize that different options may be presented to the lab operator for further processing of the containers 2.

As discussed above and shown in FIG. 1, a waste removal outlet 35 may be included in incubation chamber 5 that is separate from both the second door 9 and the first door 7. In this regard, the waste removal outlet 35 may provide an alternative for removing waste containers from the incubation chamber 5, thereby reducing interference with the transportation operations of other containers into and out of the incubation chamber 5.

Figure 4:
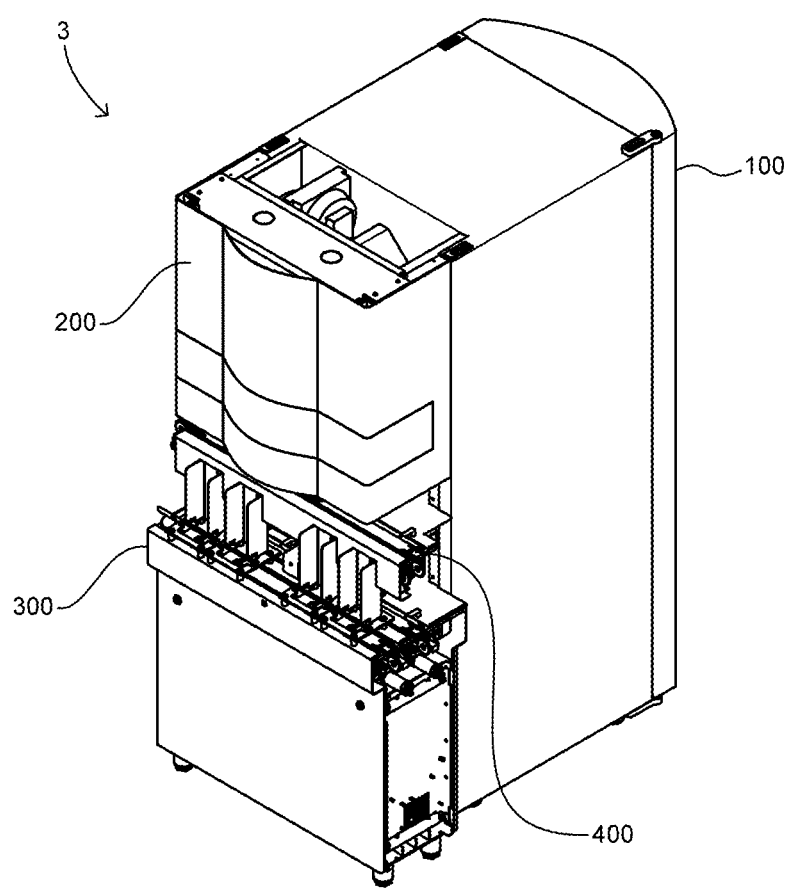
FIG. 4 is an incubator cabinet integrated with external conveyors, stackers, and an image capture module.

FIG. 4 illustrates another embodiment of the integrated incubator and image capture module 3. The integrated incubator and image capture module 3 includes the incubator 100, an image capture module 200, and a first track system 300 that receives specimens for incubation and transports them into the incubator. A second track system 400 transports containers inoculated with sample from the incubator when incubation/imaging is complete. Conveyor 300 is equipped with racks or cassettes that can receive petri dishes and hold them in a stack.

In preferred embodiments, the integrated incubator and image capture module 3 is capable of being integrated into a fully automated laboratory environment. In this regard, containers such as plates, e.g. petri dishes (illustrated), having culture media inoculated with biological fluids such as blood, urine, sputum, etc. or other biological or environmental samples for incubation and inspection are received on the first track 300. Suitable sample containers are well known to one skilled in the art and are not described in detail herein. Neither are culture media or types of samples used to inoculate the culture media. In the automated laboratory environment, there can be several integrated incubator and image capture modules, each incubator having, for example, different atmospheric conditions and settings. The first track system 300 includes a mechanism that reads information on the dish (i.e., barcode or RFID) and directs the specimen to the incubator (or the assigned incubator if more than one).

The sample container enters the incubator cabinet in integrated incubator and image capture module 3 through a first door 310 onto shelf 320 where a robotic arm (not shown) catalogs the specimen by reading a code thereon and places it on an available shelf in the incubator for a prescribed incubation time. The location of the sample container in the cabinet is associated with the sample for later retrieval of the sample.

The prescribed incubation time may be set by a lab operator. Alternatively, the incubation time may be pre-set based on certain discrete inputs such as the amount and type of sample, the target microorganism(s), the culture media, etc. In this regard, the incubator includes a processing unit (not shown) that cooperates with the robotic arm to inventory the sample containers as they enter the incubator.

The processing unit is not described in detail herein. Such units for the inventory and monitoring of samples in a cabinet type of incubator for incubation of large number of samples in containers are well known to the skilled person and not described in detail herein. Such automated systems may include one or more processors or other dedicated logic and memory for storing and tracking information related to the sample containers in the incubator. In this regard, the processing unit tracks at least the location of the specimen in the incubator, the incubation time, the number of images to be captured, the number of times the specimen is to be imaged and duration therebetween. The duration between the time a specimen is imaged, replaced back into the cabinet and removed again for imaging is referred to herein as an "imaging interval." However, one of ordinary skill in the art will appreciate that the processing unit may track additional information, such as the type of sample, the type of culture media, precautionary handling information (i.e., hazardous specimens), etc.

Information related to the samples may be stored in a database or table located in the memory of the processing unit. The one or more processors will update the information stored in the memory, accordingly. For instance, when a new sample container is received at the first door 310, the one or more processors of the system's processing unit will create a new entry in the database stored in memory. Accordingly, a start time and end time for the prescribed incubation interval may be set. Further, in preferred embodiments, the database will schedule the imaging intervals and will include an indication (i.e., timestamp, a check mark, or flag) of when the image has been captured. Alternatively, the database may include blank entries such that the actual time the sample container was imaged can be entered.

Imaging the specimens during the prescribed incubation time can occur once or, more typically, multiple times at discrete imaging intervals to obtain images of the sample container over time to determine whether or not cultures of microorganisms are growing in the sample container. The examples described herein discuss imaging specimens periodically. However, one of ordinary skill in the art would recognize that the specimens may be imaged just once (i.e., as they exit the incubator), twice (i.e., as they enter and exit the incubator), or any suitable number of times during the incubation period.

In this regard, the robotic arm retrieves the sample container from its shelf. The sample container is placed on shelf 220 before passing into the image capture module 200 through door 210. Door 210 is an example of a portal through which petri dishes are conveyed into and from the imaging module. Door 210 is referred to herein as a third door to distinguish this door 210 from first and second doors for initial ingress and final egress of petri dishes into and out of the cabinet. In this regard, each of the ports described herein may be configured with one door or with separately controlled doors, one for ingress and one for egress. For example, the third door 210 may be a dual door construction (e.g., one door for dishes entering the image capture module 200 and one door for dishes exiting the image capture module 200) or any other suitable mechanism that limits the exchange of atmosphere between the incubator and the image capture module. While embodiments herein describe configurations with at least three doors, the skilled person will appreciate that the cabinet can be further adapted to include additional ports to support additional functions that require petri dishes to be removed from and replaced in the cabinet. Such doors can also be configured to have either single or multiple ports.

The image of the sample container is captured by the imaging unit 230 of the image capture module 200. The sample then passes through third door 210 back into incubator 100, and onto interior shelf 220 where it is retrieved by the robotic arm and placed on an available shelf. Accordingly, the processing unit of the incubator may select the location of the available shelf based on the further processing planned for the dish. For example, dishes that require further image processing may be placed on an available shelf closer to the image capture module. Further, dishes that are nearing the end of their incubation time may be placed on a shelf near the second door 410.

The location of the sample container in the incubator is updated in the system. At any time, based on expiration of time, imaging results, user intervention, or the occurrence of other conditions or events detected either by sensors or operator observations, the sample container may be moved to the exit as discussed below.

As discussed above, the processing unit of the incubator will cooperate with the robotic arm and the image capturing system 200 to update the information in the database. Thus, when the image of the sample container is captured by the imaging unit 230, the processing unit receives an indication or notification that the image has been captured. The one or more processors of the processing unit will then update the image information related to the sample in the database.

One of ordinary skill in the art would recognize that image capture can occur at intervals defined by the operator, such as hourly, every six hours, once (i.e., after incubation), twice (i.e., entering the incubator and exiting the incubator), etc. In the alternative, the imaging intervals may be predetermined and associated with the sample container itself in the data base. Specifically, the nature of the sample, the media in which the sample is placed, or the target microorganism may be useful in determining how long to incubate the sample and the time intervals between image capture of the sample. For example, it may be determined that an interval of at least, e.g., six hours must elapse before the first signs of microbial growth might be detected by the imaging apparatus. In this example, when the robot first reads the bar code affixed to the sample container, the system records that the sample container is to be removed from the incubator and sent to the imaging module for imaging in six hours. When the six hours have elapsed, the robot retrieves the sample container and places it on the shelf 220 for it to be conveyed from the cabinet and into the imaging module. Furthermore, a skilled artisan will appreciate that certain samples may be incubated for more or less time as appropriate and may need to be imaged with greater or less frequency than other samples. For instance, a sample with an incubation time of twelve hours may be imaged every thirty minutes, whereas a sample with an incubation time of thirty-six hours may be imaged once an hour. Alternative incubation times and imaging intervals are a matter of choice on the part of the operator of the system. Suitable incubation times and imaging intervals are readily determined by one skilled in the art.

When the prescribed incubation time has expired or the sample is requested by a lab operator, the robotic arm retrieves the sample container from its location in the incubator cabinet and places the sample container on the cabinet shelf that supports the conveyor that conveys samples from the cabinet for removal therefrom through second door 410. The sample container passes through the second door 410 and exits the incubator where it can be retrieved by a lab operator for further analysis, sent for disposal, or sent for further analysis in an automated manner (e.g., a module or instrument engaged with the cabinet via a track or conveyor system).

In this regard, the processing unit may update the information associated with the sample container/sample in the database memory indicating that the sample container/sample has exited the incubator. That is, the processing unit may indicate that the sample specimen has completed its prescribed incubation time or is ready for further processing. Thus, the processing unit may store the entry for a predetermined amount of time after the sample specimen has completed its prescribed incubation time. Alternatively, the processing unit may forward the completed entry to a third-party where it could be stored for later retrieval.

Although the invention has been described as being used in an automated lab setting, alternative embodiments allow for a lab operator to manually feed specimens in to and receive incubated specimens from the integrated incubator and imaging module 1. Accordingly, the first track system 300 and the second track system 400 need not be present in alternative embodiments. In other embodiments, different conveyor configurations may be used when a lab operator provides the sample containers to the incubator system manually. Such track systems are well-known to one skilled in the art and will not be described in detail herein.

Figure 5A:
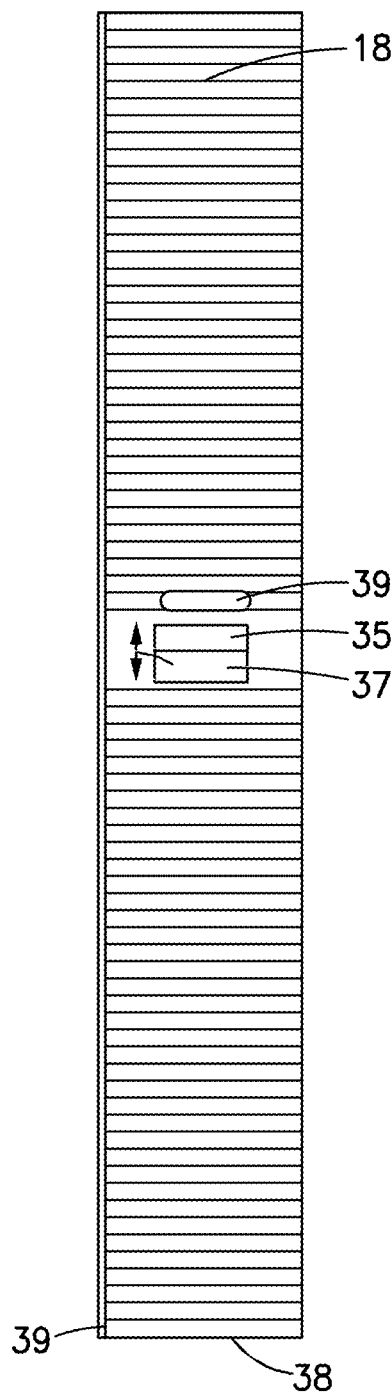
FIGS. 5A and 5B illustrate the waste removal outlet station according to one embodiment of the present invention.
Figure 5B:
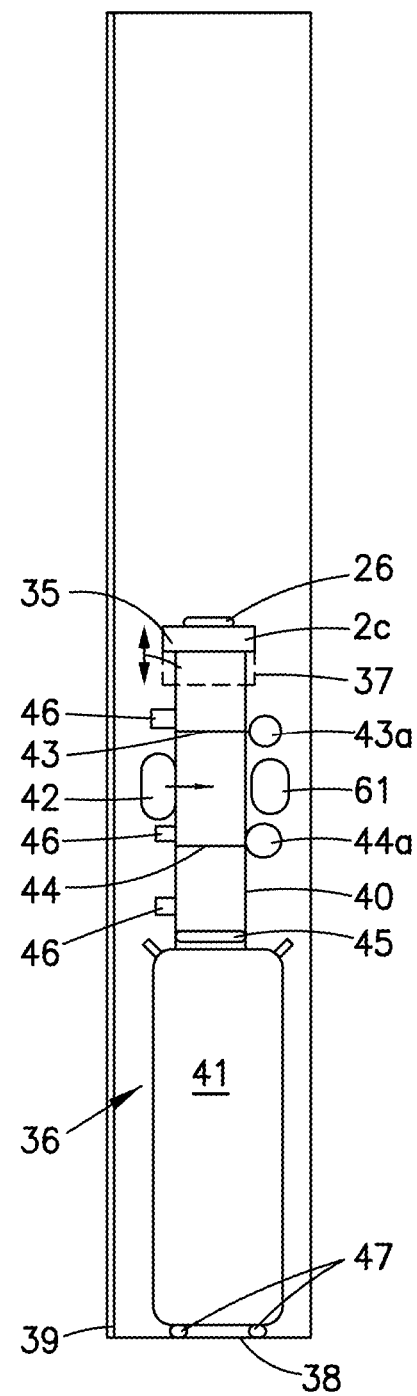

Turning to FIG. 5A, an example of a storage array 18 is shown. As discussed above, the storage arrays 18 line the inner walls of the incubation chamber 5. FIGS. 5A and 5B also show the waste removal outlet 35 that may be included in some embodiments. According to those embodiments, the waste removal outlet 35 may be a port that is sealable by a door or shutter 37, which allows a waste container 2c to be removed from the incubation chamber 5. Door or shutter 37 may be closable to prevent access into the incubation chamber 5. The microprocessor 10 may control the opening and closing of the door or shutter 37. In some embodiments, the door or shutter 37 may include a sensor (not shown) to detect the presence of the robotic arm or a container 2. In this regard, the door or shutter 37 typically opens when a sensor detects the presence of the robotic arm 20 or a container 2. Although described in the context of the operation of the door or shutter 37, all doors of the integrated incubator and imaging module can be operated in the described manner.

When included in the incubation chamber, the waste removal outlet 35 may be provided in a side of the incubation chamber 5 other than the side in which the first door 7 and the second door 9 are located. In some embodiments the waste removal outlet 35 may be located on a wall opposite of the first door 7 and the second door 9. As shown in FIG. 5A, the incubation chamber 5 is provided with a door 38 which is hinged 39 to the housing 4 for allowing access to the interior of the incubation chamber 5 and the waste removal outlet 35 may be provided in the door 38. Alternatively, the waste removal outlet 35 may be provided on a wall adjacent to the wall with the first door 7 and the second door 9.

Referring to FIG. 5A, the door 38 is illustrated from the interior of incubation chamber 5. In embodiments that include the waste removal outlet, the storage array 18 may break at the location of the waste removal outlet 35. In some embodiments, the container includes a lid. According to these embodiments, the waste removal station may include a seal applicator 39 for applying a seal to the container for sealing the lid to the container to prevent dislocation of the lid from the dish. Typically, the seal applicator may be a tape applicator for applying an adhesive tape around the dish and the lid. In alternative embodiments, the seal applicator may be an applicator to shrink-wrap the container. Alternatively, the seal applicator may apply glue or a heat weld between the lid and the container so that the lid and the dish are fixed to one another.

FIG. 5B illustrates the exterior of the door 38. According to some embodiments, door 38 may also include the waste removal outlet 35, which leads to a waste removal station 36. The waste removal station 36 may include a waste transport element 40 for transporting a waste container 2c from the waste removal outlet 35 to a waste container 41. The waste transport element 40 may include at least one sterilization component. Accordingly, the sterilization component may include a source of irradiation 61 or a gas source 42 configured to introduce a gas into the waste transport element 40. Alternatively, a washing and rinsing mechanism may be provided for certain types of containers.

In some embodiments, the waste transport element 40 may be a waste removal chute. However, FIG. 5B illustrates a waste removal tube 40 to more reliably prevent contamination. The waste removal tube 40 may include two sealable waste doors 43 and 44 with associated motor operated drives 43a and 44a. The motor operated drives 43a and 44a control doors 43 and 44, respectively, and allow a waste container 2c to pass there through. In this regard, the doors 43 and 44 are opened in stages to prevent access into an upstream part of the waste removal tube 40.

In embodiments that include the waste removal outlet, the waste removal station 36 may also include a pressure generator. For example, the gas source 42 may generate an overpressure in the waste removal tube 40 between the two sealable waste doors 43 and 44. Alternatively, the gas source 42 may reduce pressure in the waste container such that the air will flow from the environment to the waste container. In this regard, no contaminated air can escape from the waste container, thereby protecting the environment from contamination.

According to some embodiments, the waste container 41 is removable. In this regard, the waste container 41 attaches to the waste transport element 40, for example, by means of a bayonet connection. The connection means may be arranged such that upon removing the waste container 41 from the waste removal tube 40, the tube 40 is automatically closed off by a sealing door. Preferably, a double sealing door 45 is provided to seal off the door. When a new waste container 41 is connected to the tube, the sealing door 45 is arranged to open automatically.

In the embodiments that include the waste removal outlet, the waste removal station 36 may include at least one counter 46 for counting containers 2c removed from the waste removal outlet 35. This allows the waste removal station 37 to track the correct removal of containers and to provide an indication when the waste container 41 is expected to be full.

In alternative embodiments, a reader 26 maybe be proximately located to the waste removal outlet 35 to keep track of the containers 2c. Typically, the waste container 41 is configured to be mobile to be moved between integrated incubator and image capture modules 3. For example the waste container 41 may be provided with wheels 47 or any suitable means for transporting the waste container 41 between the integrated incubator and image capture modules 3.

Although the embodiments described herein refer to a waste removal tube 40 through which the cell culture devices are passed under the influence of gravity, a more controlled removal of waste containers can be realized in alternative embodiments. For example, the waste transport element may include a motor configured to operate a waste removal conveyor, such as an elevator or stacker. The microprocessor 10 may control the waste removal conveyor to control the discharging waste containers from the waste removal outlet to the waste container.

In other embodiments, the waste removal outlet may be omitted from the door 38. Accordingly, the microprocessor 10 may direct the robotic arm 20 to discharge the container 2c via the second door 9. In this regard, the robotic arm may remove container 2c from its shelf and place it on the shelf to be transferred to the second track system. The container 2c may then traverse the second track system 400 until reaching a sorting unit (not shown). Accordingly, the sorting unit may route the container 2c to a disposal area. Alternatively, the sorting unit may direct the container 2c to a rack where the containers can be disposed of by a lab technician.

FIGS. 7A and 7B illustrate front view and side views of the integrated incubator and image capture module 3, with the imaging module disposed on what is designated the front of the cabinet. The illustrated conveyers 300 and 400 allow the integrated incubator/imaging module 3 to be incorporated in an automated lab setting. As described above, the first track system 300 includes a first door 310 where sample containers, such as petri dishes and other specimen containers, enter the incubator. First track system 300 interconnects with a series of other tracks or other automated lab equipment to allow for the movement of petri dishes through the automated lab. Although the sample container is described as a petri dish in the description of the several embodiments herein, the skilled person will appreciate that the apparatus described herein is readily adapted to handle other types of sample containers.

FIGS. 7A and 7B illustrate the image capture module 200 as placed near the top of the integrated incubator image capture module 3. The petri dishes are conveyed from the cabinet and through door 210 via the conveyor supported by shelf 220. The petri dishes are returned to the cabinet through the same door 210 via the conveyor supported by shelf 220. In this regard, the door 210 is configured to allow the sample container (e.g. petri dish) to be conveyed through it when opened, but is not significantly larger than the sample container to minimize loss of controlled atmosphere from the cabinet when the door is opened.

Furthermore, image capture module 200 is a contained unit immediately adjacent the incubator that keeps the door 210 separated from the ambient laboratory atmosphere.

In preferred embodiments, image capture module 200 includes high-efficiency particulate absorption (HEPA) filters to keep contaminants that are present in the lab ambient atmosphere from contaminating the samples conveyed to and from the image capture module/incubator cabinet. In alternative embodiments, other devices may be used to prevent contaminants from entering the image capture module 200, such as UV lights or a series of filters with varying degrees of granularity. One of ordinary skill in the art would recognize that the contaminant prevention mechanisms described herein may be used on their own or in combination with other filtering equipment.

Preferred embodiments of the image capture module 200 may also include insulation to reduce heat loss from the incubator environment to the laboratory atmosphere through the image capture module 200. Alternatively, the image capture module 200 includes seals to further reduce the extent to which the lab atmosphere might enter the image capture module and contaminate the sample containers conveyed there through or enter into the incubator as the sample containers are transferred from the incubator to the image capture module. Thus, the image capture module 200 incorporates the use of filters and insulating materials to reduce contamination of the sample containers during image capture.

FIGS. 7A and 7B also illustrate door 410 where petri dishes and other specimens exit the incubator onto the second conveyor system 400. It is important to note that doors 210, 310, and 410, located on the face of the incubator, are configured to permit sample containers to be automatically conveyed in and out of the incubator cabinet. Therefore, these doors or ports are substantially smaller in size than a door located on another side of the cabinet that allows operator access to the interior of the cabinet. Such a large door can be disposed on any side of the cabinet. In preferred embodiments, the size of the doors is slightly bigger than the size of a petri dish and is largely a matter of design choice. As noted above, it is preferred that the doors be no larger than necessary to keep the interior environment of the incubator as stable as possible as sample containers are conveyed in and out of the cabinet. Alternative embodiments contemplate door sizes that are approximately 1½ inches high by 3 inches wide.

Figure 8:
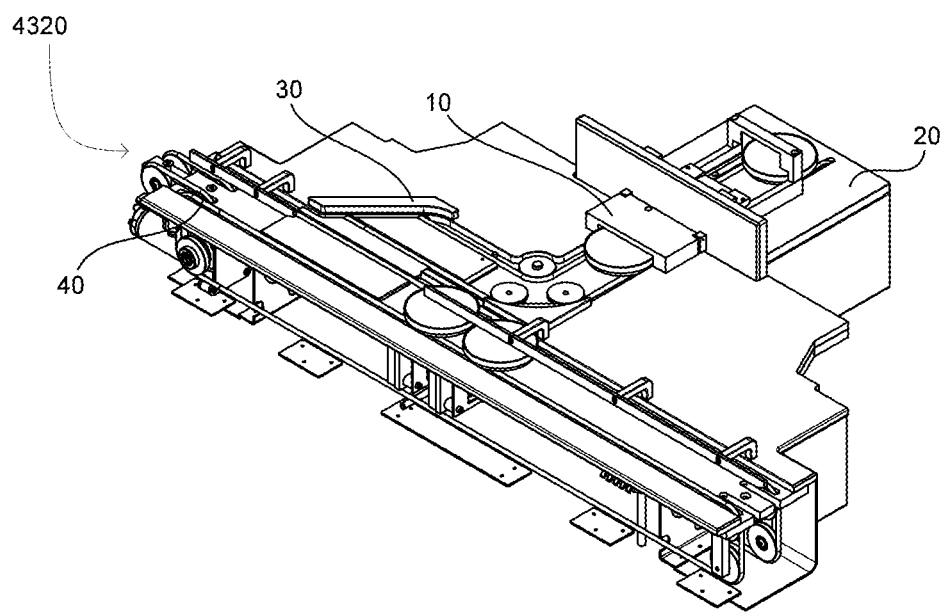
FIG. 8 is a perspective view of a conveyor portion that permits petri dishes to be automatically conveyed out of the incubator cabinet through a door disposed in the cabinet housing.

FIG. 8 shows an example of a conveyor module 4320 that serves to transport sample containers (petri dishes are illustrated). In various configurations, the conveyor module 4320 can feed sample containers both into and out of the incubator cabinet through doors 310 and 410. In the context of the first conveyor system 300, conveyor module 4320 has a conveyor system 40 that can cooperate with other conveyors to convey the petri dishes among the various stations in the automated lab. Conveying systems such as those illustrated herein are well known to one skilled in the art and are not described in detail herein. Adjacent to conveyor system 40 is a device (no shown), such as a bar code scanner or RFID reader, for reading identification data in the form of a bar code on the petri dishes that are conveyed by the conveyor module 4320. One of ordinary skill in the art would recognize that alternative device readers/identification tags could be used in place of a bar code scanner or the RFID reader.

When a bar code on a petri dish is read by the scanner or reader and the system determines that the petri dish is to be directed from the cabinet of the integrated incubator and image capture module 3 a signal is sent to switching mechanism 30 to direct the petri dish from the assigned cabinet. In this regard, switching mechanism 30 diverts the selected petri dish from incubator door 10 to the conveyor system 40. The petri dish passes through the door 10 from the incubator shelf 20, where the petri dish is catalogued by a reader (e.g. a bar code reader, RFID reader, etc.) which communicates with a processor to update the processor on the location of the petri dish.

In the context of the second conveyor system 400 (FIGS. 7A-B), the robotic arm (not shown) is directed to place the petri dish on shelf 420 when the processor has determined that the petri dish has completed its prescribed incubation time or is requested by a lab operator or is indicated to be ready for downstream processing. In this regard, the processor may advantageously update information related to the petri dish with respect to the further processing of the petri dish. That is, the incubation system may advantageously communicate with other components of the automated lab, and in particular the conveyor system, to indicate further processing of the petri dish. As noted above, the system contemplates full automation in delivering samples to the incubator, transporting and storing them in the incubator, temporarily removing the petri dishes to the imaging system, returning the samples to the incubator for further growth and subsequent further inspection and transporting the petri dishes from the incubator for further processing, inspection or disposal. Conveyors and other mechanisms for conveying petri dishes to and from the incubator are well known to one skilled in the art and not described in detail herein With reference to FIG. 8, in one embodiment of those aspects of the system where the petri dish is conveyed from the cabinet, the conveyor, supported by shelf 20 conveys the petri dish through door 10 onto conveyor module 4320. The switching mechanism 30 directs the petri dish onto the main portion of the conveyor system 40. The conveyor system for both conveying petri dishes toward the cabinet and away from the cabinet, shown in FIGS. 1, 2A, and 2B, are configured such that the petri dishes do not collide or otherwise interfere with one another as they are being transported.

Once the petri dish is on the conveyor module 4320 it may be transported downstream for further processing. Typically, the incubated petri dishes will be conveyed to a stacking conveyor system module as discussed in greater detail below. In some embodiments, the incubated petri dishes may be conveyed downstream for further processing, such as inoculating a different media with the cell growth, tracking the size of the colony, enzyme detection, etc. Other downstream processing techniques would be readily apparent to those skilled in the art and are not discussed in further detail herein.

Additionally, the conveyor system may transport incubated petri dishes to a disposal area. Typically, when no culture growth has been detected by either the imaging analysis unit or the lab operator or both, the plate may be conveyed to the disposal area. The disposal area may also be a stacking system as described in greater detail below, where petri dishes are retrieved by a lab operator and disposed of accordingly. Alternatively, petri dishes may be advantageously conveyed to a biohazard waste receptacle.

Figure 9:
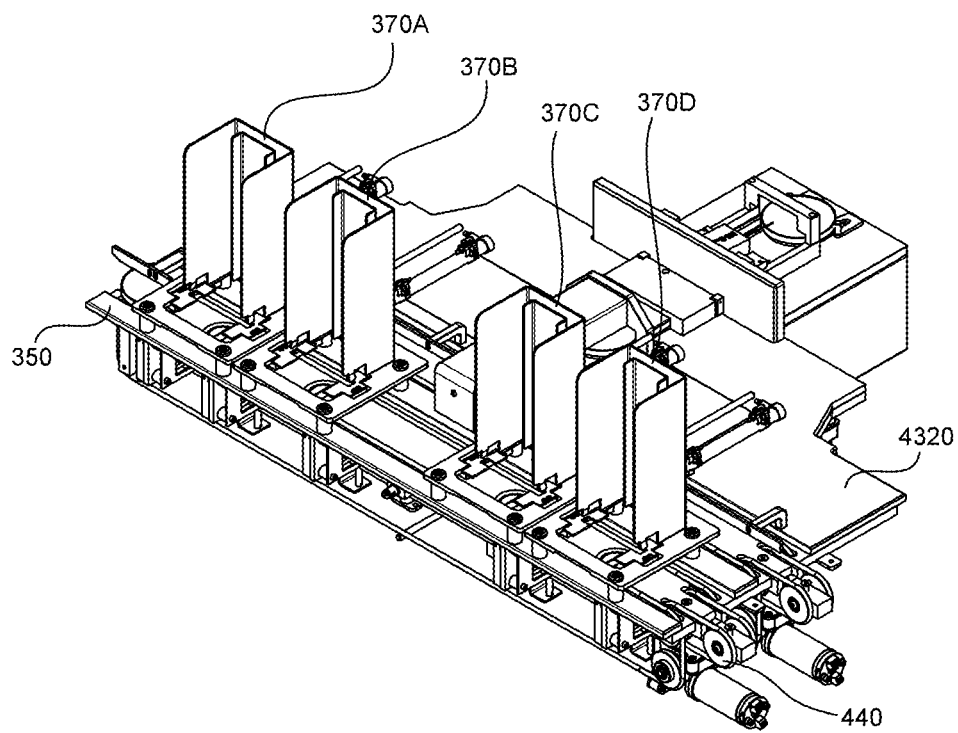
FIG. 9 is a perspective view of a conveyor portion with a stacking conveyor system for moving petri dishes into the incubator and stacking them for further handling.

FIG. 9 illustrates a stacking conveyor system module 350 that connects to conveyor module 4320. Stacking conveyor system 350 has a conveyor system 440 (as described above with respect to FIGS. 1, 2A, 2B) that runs in a direction parallel to the direction of conveyor system 40 of conveyor module 4320. Stacking conveyor system 350 has a series of racks 370 that store petri dishes in stacks disposed in the racks. Although FIG. 9 illustrates four racks 370A, 370B, 370C, and 370D, one of ordinary skill in the art would appreciate that the stacking conveyor system 350 can have more or fewer racks.

In operation, petri dishes are conveyed along conveyor system 440. In this regard, the system comprises a plurality of dish stopping units (not shown). The system tracks the progress of the dish through the conveyor system. Therefore, when a petri dish is determined by the system to be beneath the appropriate rack (the particular rack selected will depend on why the petri dish was removed; e.g., for further processing, disposal, etc.), the system sends signals that will cause the petri dish to be loaded into one of the racks 370A, 370B, 370C, or 370D. To accomplish this, the conveyor system 440 is provided with a mechanism that places the petri dish into its assigned rack. The racks 370A, 370B, 370C, and 370D include a one-way gate that allows petri dishes to pass into the racks and holds them in the rack to prevent them from falling back onto conveyor system 440. In preferred embodiments, the racks 370A, 370B, 370C, and 370D can hold up to 20 petri dishes. Stacking dishes significantly higher than 20 creates a greater risk of the dishes toppling, which would ruin the sample, create a contamination risk, etc.

The stacking conveyor system 350 automates sample container collection from the integrated incubator and image capture module 3 or any other suitable automated lab equipment, for example an automated inoculation system such as the one described in U.S. Provisional Patent Application No. 61/973,551 filed on Apr. 1, 2014 and entitled "System and Method for the Automated Preparation of Biological Samples" which is commonly assigned with the present application and hereby incorporated by reference. Using the stacking conveyor, sample containers can be collected in predetermined order and stacked in such order for retrieval by a lab operator. Such automated tools reduces the amount to which the interior of the cabinet needs to be accessed, thereby preserving the environment inside the cabinet.

In some embodiments, one of the racks 370A, 370B, 370C, or 370D may be dedicated to receiving plates for disposal. As discussed above, plates that did not exhibit culture growth, or were otherwise defective, may be collected in one of the dedicated racks to be disposed of by the lab operator in a safe manner or disposed through the waste door 37 as previously described.

Alternatively, the processor 10 may send signals to the conveyor system to convey the incubated dish for further downstream processing. As discussed above, this may include inoculating other media with the culture growth, image analysis of the plate, enzyme analysis, etc. Additionally, the conveyor system may automatically direct the incubated plates to an automatic disposal unit (not shown).

Figure 10:
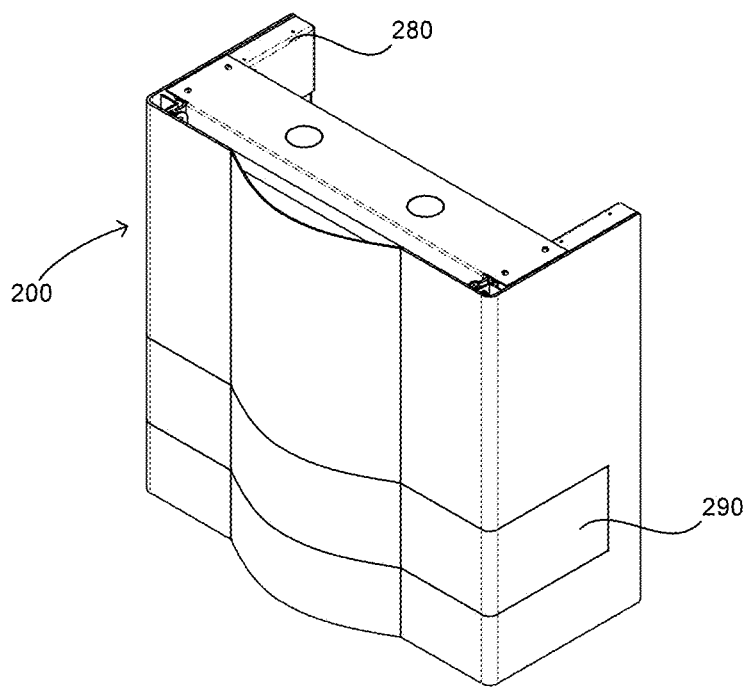
FIG. 10 is an exterior perspective view of the housing of the image capture module.

The housing for the image capture module 200 is shown in FIG. 10. Image capture module 200 housing has a transparent portion 290 that permits a lab operator to view the operation of the image capture module 200. Additionally, the housing has filters 280 disposed therein to prevent contaminants from entering the interior portions of the image capture module 200. As discussed above, the filters 280 are preferably HEPA filters. However, the filters 280 may be a series of filters, one of which may be a HEPA filter, or UV lights that neutralize contaminants. One of ordinary skill in the art would recognize that any suitable filter capable of capturing contaminants from entering the module or escaping therefrom could be used. Furthermore, a skilled artisan would recognize that the filter mechanisms described herein could be used individually or in combination.

Figure 11:
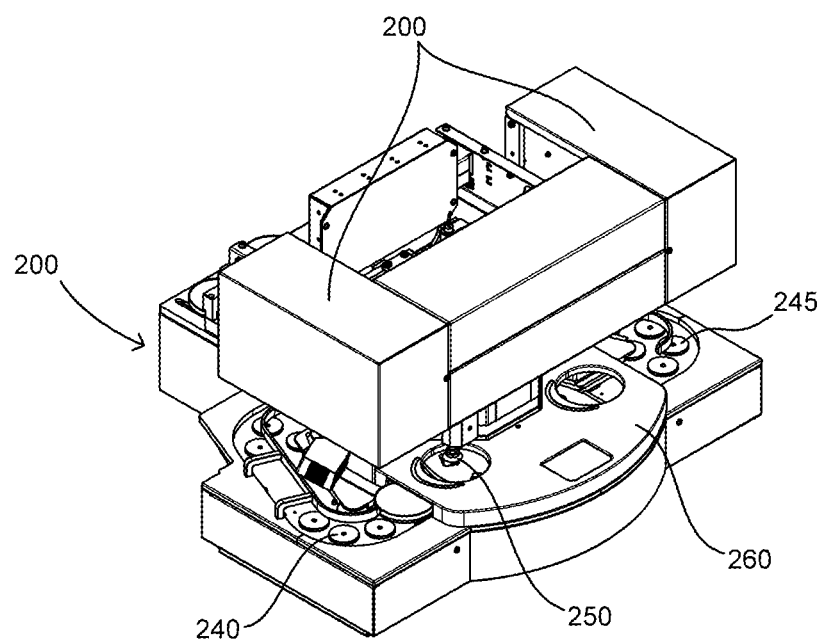
FIG. 11 is a perspective view of an interior portion of the image capture module which illustrates the conveyor from the incubating system, through the imaging unit and back to the incubator.

Referring to FIGS. 11-16, the image capture module 200 is shown with petri dishes passing through in various stages of being imaged. As discussed above, a petri dish is transported through door 210 and into the image capture module 200. As illustrated in FIG. 11, the petri dish travels along conveyor system 240. The petri dish reaches a location it is read by a reader (i.e. bar code scanner or RFID reader). The petri dish is then placed back on the conveyor system 240, where it then moves the dish onto rotating carousel tray 255. The lid manipulator 250 subsequently removes the lid of the petri dish. Rotating carousel tray 255 moves the petri dish into position under image capture unit 230, which will be described in further detail below.

Once an image of the petri dish is captured by image capture unit 230, the rotating carousel tray 255 rotates the dish to a post-processing position. In the post-processing position, the lid is replaced on top of the petri dish and the petri dish is placed on conveyor system 245. The conveyor system 245 returns the petri dish to the shelf 220 in incubator 100 through door 210. Once on the shelf 220, the petri dish label is read and the robotic arm, in response to instructions from the processor, retrieves the petri dish and places the petri dish on an available shelf to continue incubation, with the system updated with the location of the petri dish in the cabinet, or relocated to the exit mechanism if the system is so instructed. As discussed above, information regarding the placement and processing history of the petri dish as it is transported through the image capture module is maintained in the processing unit of the incubator.

Figure 12A:
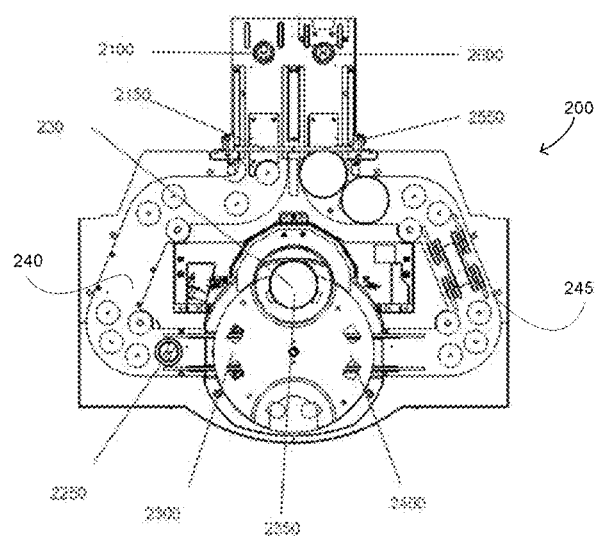
FIGS. 12A and 12B are cut away top plan views of the image capture module.
Figure 12B:
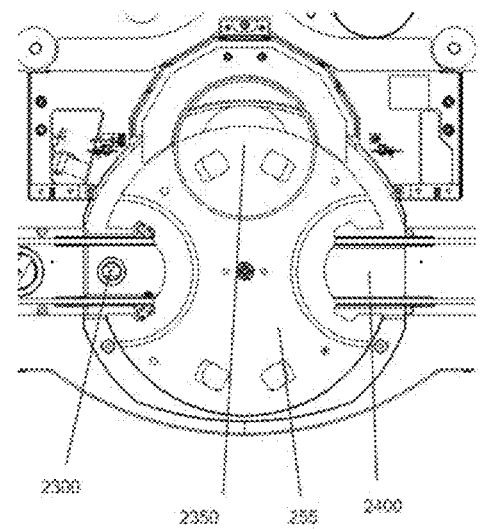

The movement of the petri dish through the image capture module 200 is illustrated in FIGS. 12A and 12B. At position 2100, the robotic arm places the petri dish (not shown) that has been selected for imaging on shelf 220. In position 2150, the petri dish is conveyed through door 210 by way of the conveyor 240 of the image capture module 200. The conveyor 240 moves the petri dish to location 2250 where it is rotated and catalogued by a reader (e.g. bar code or RFID). The petri dish is then rotated and moved on conveyor 240 to location 2300, where the lid manipulator unit 250 removes the lid from the petri dish. The rotating carousel tray 255 then moves the petri dish into position under the image capture unit 230. The image capturing unit 230 captures a digital image of the petri dish at location 2350. Equipment for the capture of digital images of plated cultures is well known to one skilled in the art and is not described in detail herein.

At location 2350, the integrated incubator and image capture module 3 optionally displays the captured digital image of the cultured sample on a display (not shown) for review. The processing unit may also save the image electronically. Devices for storing digital information, e.g., servers, storage systems and devices, memory devices, etc. are well known to one skilled in the art and not described in detail herein. In alternative embodiments, the digital image is analyzed using a software program that can determine, based on prior information/images of the petri dish if microbial growth has occurred. Such programs for digital inspection of the culture to detect changes indicative of microbial growth are known to the skilled person and not described in detail herein. Once such program is described in U.S. Provisional Patent Application No. 61/933,426 filed on Jan. 30, 2014 and entitled "A System and Method for Image Acquisition Using Supervised High Quality Imaging" which is commonly assigned with the present application and hereby incorporated by reference. Upon automatic digital inspection of the captured image the processor can alert a lab operator of any abnormalities, such as rapid culture growth or other anomalies. Additionally, the captured image may be displayed for the lab operator's review at the appropriate time along with prior images of the plate for visual comparison by the operator in addition to or as a substitute for digital analysis of the captured image using the digital image analysis.

Once the digital image of the plated culture is captured by the imaging unit at location 2350, the rotating carousel tray 255 carries the petri dish to the post-processing phase at location 2400. At location 2400 the lid is placed back on top of the petri dish and transferred to conveyor system 245. The conveyor system 245 conveys the petri dish to door 210 at location 2550. There, the petri dish is conveyed through door 210 and onto shelf 220. There the petri dish tag is again read, and the processor controls the incubator's robotic arm 20, at location 2600, to retrieve the petri dish and place it on an available shelf, or move it to the exit mechanism if so instructed. The location of the petri dish is updated in the system. The petri dish continues to reside at this location while further incubating for its prescribed incubation time. As discussed above, information regarding the status of the petri dish as it passes through the image capture module and back into the incubator cabinet is continually updated so that the information regarding the status and analysis of the petri dish and the plated culture within the dish is continuously updated by the system using the central processing unit of the incubator.

Figure 13:
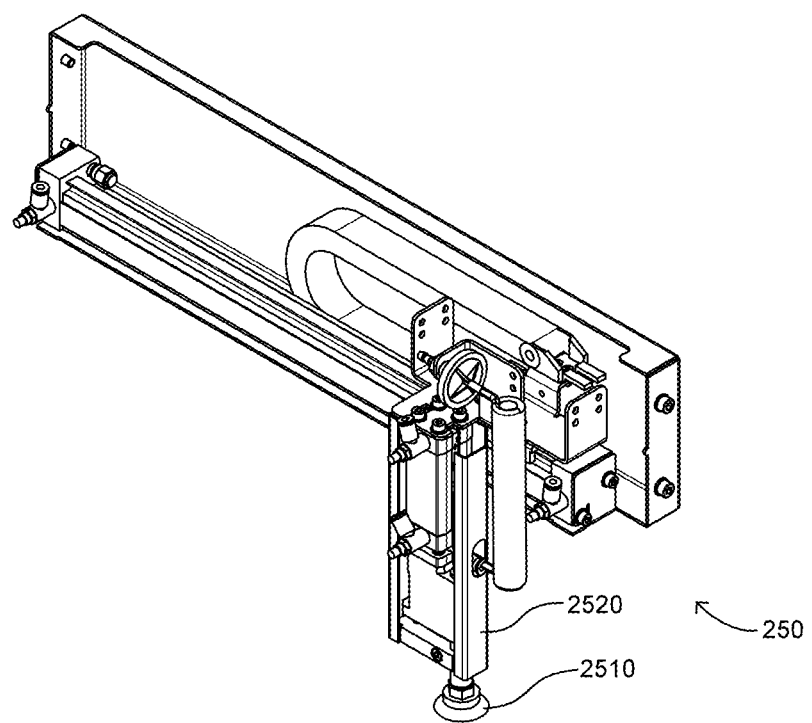
FIG. 13 is an illustration of a lid manipulator unit.

Referring to FIG. 13, the lid manipulator unit 250 is shown in greater detail. The lid manipulator unit 250 includes an arm 2520 that moves a manipulator unit 2510 vertically. The manipulator unit 2510 is lowered over a lid of the petri dish by the arm 2520 until it makes contact with the lid of the dish. The manipulator unit 2520 then lifts the lid off the dish using a suctioning pad. The dish is subsequently loaded into the rotating tray 255 for image processing. Optionally, both the lid and the dish are tagged so that the lid can be accurately replaced onto its respective dish after imaging. Placing the wrong lid on the petri dish can result in cross contamination.

In some embodiments, there is a second lid manipulator unit for replacing the lid on top of the petri dish after the image processing in step 2400. However, the same lid manipulator unit may be used to remove and replace the lid on the petri dish before and after image processing. The lid manipulator unit 250 is not described in detail herein, and the skilled person will appreciate that this function can be performed in a variety of ways. In one embodiment the lid manipulator unit includes at least one motor that moves the manipulator into a position where it can both remove and replace the lid. In other embodiments, the lid manipulator 250 may be driven by a pneumatic system or any other suitable means for moving the manipulator to its intended locations.

In one embodiment the manipulator unit 2510 is a suctioning device. In alternative embodiments, manipulator unit could include a claw, a hook, or any other suitable means for lifting off and replacing a lid on the container or receptacle (e.g. the petri dish) without disturbing the growth of the cultures.

Figure 14:
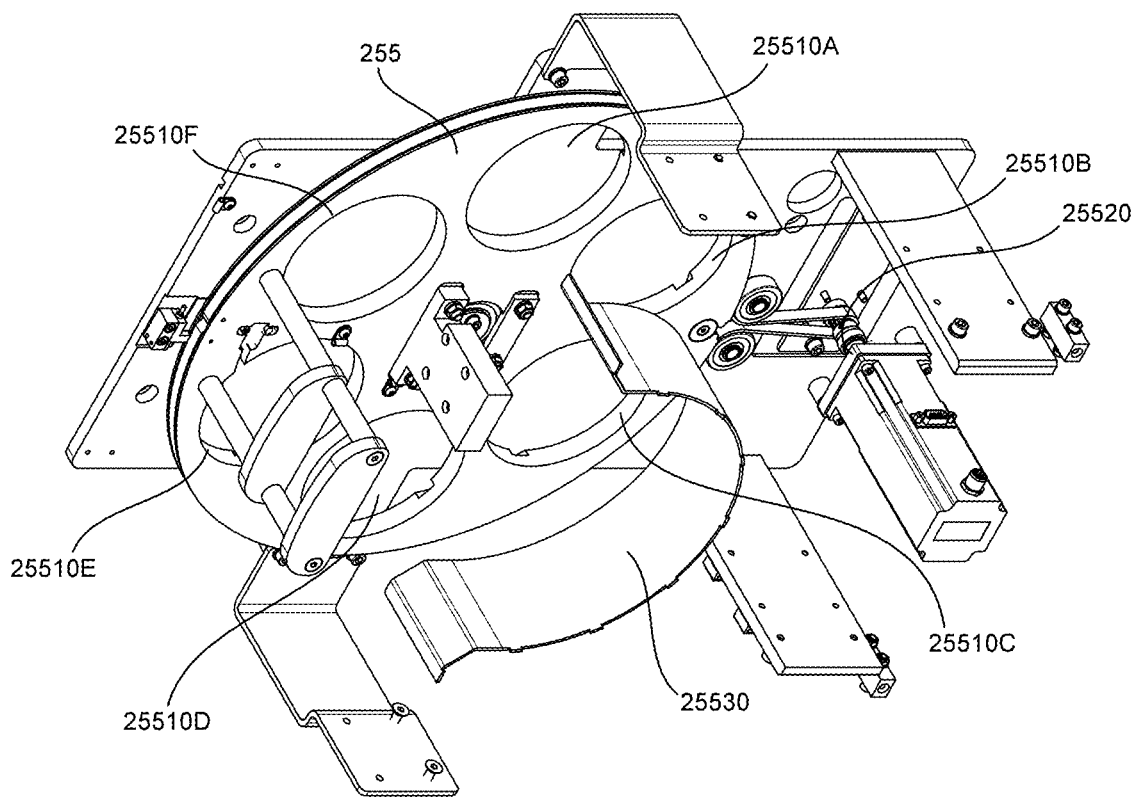
FIG. 14 is a bottom perspective view of the conveyor in the image capture module illustrating a mechanism that moves the petri dish into position for image capture.

Turning to FIG. 14, the rotating carousel tray 255 that transports the dish into position for image capture is shown. In preferred embodiments, rotating carousel tray 255 has two available receptacles 25510A and 25510B that receive petri dishes. Additionally, the rotating carousel tray includes a pneumatic cylinder 25520 to drive the rotating carousel tray 255. Alternatively the rotating carousel tray may be driven by a motor. Further, the rotating carousel includes a shelf 25530 that supports the image capture unit 230.

The receptacles 25510A and 25510B help to streamline the process of loading and off-loading the petri dishes for image capture. Although the illustrated embodiment describes two receptacles, one of ordinary skill in the art would recognize that the rotating carousel tray 255 may have any number of receptacles depending on the size of the sample containers and the imaging module.

In operation, a petri dish is loaded into one of the receptacles 25510. In the illustrated embodiment, there are two receptacles 25510 each which can receive one petri dish, one being loaded and one being unloaded. Alternative embodiments contemplate the use of more than two receptacles. For example, one plate may be loaded into the carousel tray 255 for image processing while another plate is being removed from the carousel tray 255 after being photographed; a third plate may be located under the image capturing unit 230; and the last plate may be in a holding position, either waiting to be photographed or just having its photograph taken.

The pneumatic cylinder 25520 drives the rotation of the carousel tray 255. That is, the pneumatic cylinder 25520 moves the receptacles 25510 into locations where the dishes can be placed into or removed from a receptacle. Moreover, the pneumatic cylinder 25520 rotates the carousel tray 255 such that petri dishes may be photographed by image capture unit 230. In this manner the dishes rotate through the image processing steps discussed above with respect to FIG. 12.

Figure 15:
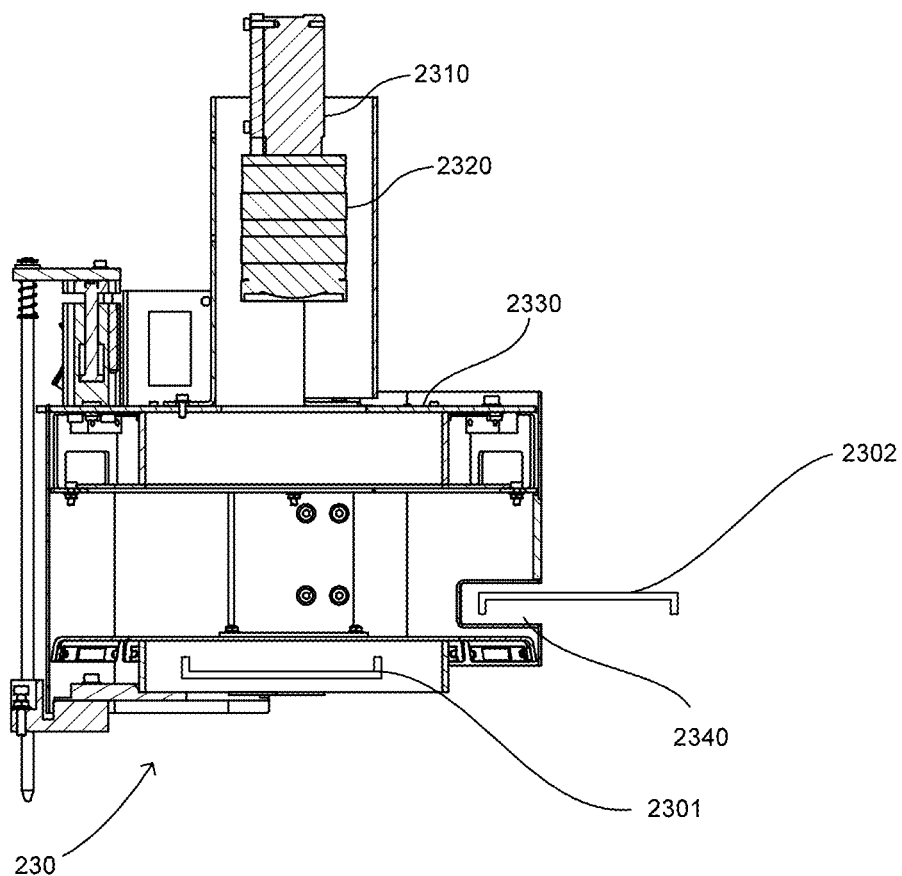
FIG. 15 is a cut away side view of one embodiment of the image capture component of the imaging unit.

FIG. 15 shows one embodiment of an image capture unit 230. Image capture unit 230 includes an image sensor unit 2310, a lens unit 2320, at least one light source 2330, and a channel 2340 for lids to pass. Alternatively, the image capture unit 230 may not include a channel 2340.

In one embodiment, the image sensor 2310 is a high-resolution image sensor, such as a charge-coupled device (CCD). However, any suitable image sensor may be used, including CMOS or NMOS image sensors. Such sensors are well known to one skilled in the art and are not described in detail herein. While only one image sensor unit 2310 is shown in FIG. 15, one of ordinary skill in the art would recognize that several image sensor units, of varying types, may be used. In this regard, multiple images may be captured from a variety of positions or angles. Further, images may be captured at different wavelengths.

Image capture unit 230 also includes a lens 2320. In one embodiment, the lens is a 16 millimeter lens. However, one of ordinary skill would recognize that any suitable lens could be used in conjunction with the image sensor 2310. Such lenses are well known to those skilled in the art and are not described in detail herein.

Additionally, image capture unit 230 has at least one light source 2330. The light source directs light to illuminate the sample containers for image capture. In preferred embodiments, the light source 2330 is one or more light emitting diodes (LEDs). In certain embodiments, wavelengths of light are selected to provide an image across the visual spectrum. Any suitable light source may be used to illuminate the petri dish for image capture. In some embodiments, light source 2330 has at least three individual light sources that emit at the same or different wavelength ranges. It is contemplated that any number of light sources may be used to provide illuminating light suitable for imaging the cultures. Illuminating light can be directed onto the sample from a variety of directions which are largely a matter of design choice, depending upon, among other things, the orientation of the image capture apparatus and other optics of the system. In alternate embodiments, the light source 2330 may be located above, to the side, or beneath the petri dish to illuminate the petri dish for image capture. In other embodiments, the light is directed onto the sample from multiple different directions. Accordingly, the light source 2330 may be included that illuminates the petri dish from both above and below to provide the appropriate amount of light so that the image capture unit can capture an image of the specimen In some embodiments, the lid manipulator 250 will remove the lid 2302 from the dish 2301. The dish 2301 will then be placed into one of the receptacles 25510 of the carousel tray 255. As discussed above, the carousel tray 255 will convey the dish through image processing. Meanwhile, the lid manipulator 250 is moving dish 2301's lid over the carousel tray 255, through the channel 2340, and to the location where the lid will be placed back on dish 2301. In this regard, channel 2340 allows for linear movement of the lid to its final destination, thereby providing the most efficient and direct route to replacing the lid back on the dish.

Figure 16:
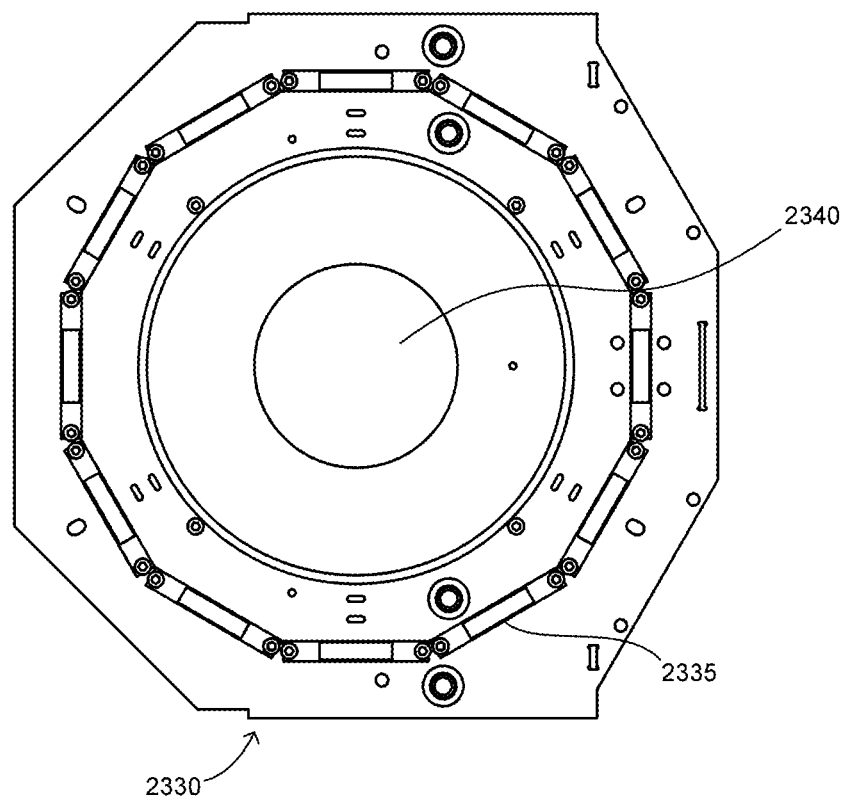
FIG. 16 is a top down view of a light source disposed above the petri dish containers for the image capture unit according to an embodiment of the present invention.

Referring to FIG. 16, an exemplary embodiment of the light source 2330 is shown. In preferred embodiments, the light source 2330 has several LEDs 2335. The LEDs 335 are arranged as a dodecagon with six groups of two LEDs each (i.e., twelve rectangular white LEDs total). In one embodiment, the LEDs are operated in groups of two, so that light may be controlled from six different directions. However, arrangements of LEDs to obtain the desired imaging are largely a matter of design choice. Suitable alternative geometric LED arrangements include hexagonal, octagonal, circular, triangular, and square arrangements.

In other embodiments, the light source 2330 is configured to be connected to the image capture unit 230 in such a way that it directs light to the sample container from either one direction or a variety of directions. As noted above, the image capture unit 230 may also include a light source that is above, to the side, or beneath the petri dish to illuminate the dish. In other embodiments, the light source may be included that illuminates the petri dish from both above and below to provide the appropriate amount of light so that the image capture unit can capture an image of the specimen.

In preferred embodiments, the light source 2330 has a center aperture 2340 through which the image of the petri dish is captured by the camera. In this regard, the camera is mounted at a certain distance from the petri dish based on a variety of factors, such as optical distortion, reflection of the light source, etc. The aperture allows the camera to be positioned at a predetermined distance from the petri dish without the LED plate blocking the camera's angle of view.

Although the invention herein has been described with reference to particular embodiments, it is to be understood that these embodiments are merely illustrative of the principles and applications of the present invention. It is therefore to be understood that these and various other omissions, additions, and numerous modifications may be made to the illustrative embodiments and that other arrangements may be devised without departing from the spirit and scope of the present invention as defined by the appended claims.

The invention claimed is:

1. A method for incubating and monitoring biological samples disposed in a culture media, the method comprising:
   conveying a sample containers into an incubator comprising a cabinet with multiple sealable ports for automated receipt and removal of the sample containers from the cabinet, wherein the multiple sealable ports includes a first sealable port, a second sealable port, and a third sealable port, wherein the first, second, and third sealable ports are vertically spaced apart on a single face of the cabinet;
   maintaining a controlled temperature environment and a controlled atmosphere composition for the sample containers in the cabinet;
   receiving, through the first sealable port the sample containers from a first conveyor adapted to cooperate with the first sealable port to receive the sample containers containing biological samples inoculated with a sample for incubation into the cabinet;
   receiving, through the second sealable port the sample containers from a second conveyor that conveys the sample containers from the cabinet;
   conveying the sample containers from the cabinet through the third sealable port via an image capture conveyor in an image capture module disposed in a housing separate from the cabinet,
   conveying the sample containers via the image capture conveyer to a rotating carousel in the image capture module, wherein the rotating carousel has a plurality of receptacles, each for receiving a sample container of the sample containers; and
   wherein the rotating carousel moves the sample containers from a location where the sample containers are received by the rotating carousel, to an image capture position of an imaging unit in the image capture module, wherein the imaging unit comprises an image sensor, a lens and a light source;
   obtaining an image of the biological samples in the sample containers at the image capture position; and
   conveying the sample containers from the rotating carousel to the image capture conveyor and through the third sealable port to the cabinet after the image capture module obtains the image of the biological samples in the sample containers, wherein the third sealable port is an only port into the image capture module from the cabinet, and further wherein the first, second and third sealable ports are sealable by first, second and third doors.

2. The method of claim 1, wherein the third sealable port further comprises:
   a sealable ingress port adapted to receive the sample containers into the image capture module from the cabinet prior to imaging of the sample containers; and
   a sealable egress port adapted to transport the sample containers from the image capture module to the cabinet after imaging of the sample containers.

3. The method of claim 1, further comprising automatically opening a door that sealably closes the first sealable port when the first conveyer conveys the sample containers to the first sealable port for placement in the cabinet.

4. The method of claim 1, further comprising a processor configured to control conveying the sample containers within the cabinet and through the first, second, and third sealable ports according to instructions communicated to the processor.

5. The method of claim 4, further comprising a memory in communication with the processor, wherein the memory receives information related to placement of the sample containers in the cabinet and provides such information to permit the sample containers to be located in the cabinet for processing.

6. The method of claim 5, further comprising at least one of:
   i) receiving the sample containers into the cabinet conveyed through the first sealable port and placing them in an available location in the cabinet for subsequent retrieval;
   ii) removing the sample containers from their location in the cabinet and placing them at the second sealable port to be conveyed from the cabinet;
   iii) removing the sample containers from their location in the cabinet and placing them at the third sealable port to be conveyed from the cabinet for image capture;
   iv) receiving the sample containers into the cabinet at the third sealable port subsequent to image capture and placing them back into an available location in the cabinet; and
   v) transporting the sample containers from a first position in the cabinet to a second position in the cabinet.

7. The method of claim 6, further comprising a robotic arm, in communication with the processor and the memory, comprising a gripper and a translation arm for gripping and moving the sample containers for performing at least one of:
   i) receiving the sample containers conveyed through the first sealable port and placing them in an available location in the cabinet for subsequent retrieval;
   ii) removing the sample containers from their location in the cabinet and placing them at the second sealable port to be conveyed from the cabinet;
   iii) removing the sample containers from their location in the cabinet and placing them at the third sealable port to be conveyed from the cabinet for image capture;
   iv) receiving the sample containers at the third sealable port subsequent to image capture and placing them back into an available location in the cabinet; and v) transporting the sample containers from a first position in the cabinet to a second position in the cabinet.

8. The method of claim 1, wherein the image capture module is adjacent to the incubator and outside the cabinet.

9. The method of claim 1, further comprising:
automatically removing a lid from the sample containers prior to image capture of the sample containers, further comprising a lid manipulator unit comprising an arm, the method further comprising moving the lid manipulator unit vertically, and the lid manipulator unit comprising a suction pad.

10. The method of claim 9, further comprising placing a lid onto the sample containers after image capture of the sample containers without the lid thereon using the lid manipulator unit.

11. The method of claim 1, further comprising illuminating the sample containers for image capture using a light source.

12. The method of claim 11, wherein the light source comprises at least one light emitting diode (LED).

13. The method of claim 1, further comprising:
sorting the sample containers according to pre-programmed categories after being removed from the incubator, wherein the sorting is performed by a stacking conveyor system, wherein the stacking conveyor system comprises a series of racks.

* * * * *